(12) United States Patent
Buck et al.

(10) Patent No.: US 6,544,181 B1
(45) Date of Patent: *Apr. 8, 2003

(54) METHOD AND APPARATUS FOR MEASURING VOLUME FLOW AND AREA FOR A DYNAMIC ORIFICE

(75) Inventors: Thomas Buck, Cambridge, MA (US); Robert A. Levine, Brookline, MA (US); Ronald A. Mucci, Warwick, RI (US)

(73) Assignees: The General Hospital Corporation, Boston, MA (US); Agilent Technologies, Palo Alto, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/467,165

(22) Filed: Dec. 20, 1999

Related U.S. Application Data
(60) Provisional application No. 60/122,926, filed on Mar. 5, 1999.

(51) Int. Cl.[7] ................................................. A61B 8/02
(52) U.S. Cl. ...................... 600/455; 600/453; 600/454; 600/456; 73/861.25
(58) Field of Search ............................... 600/453–456, 600/443; 73/861.25

(56) References Cited

U.S. PATENT DOCUMENTS

| | | | |
|---|---|---|---|
| 4,259,870 A | * 4/1981 | McLeod et al. | 600/456 |
| 4,807,636 A | * 2/1989 | Skidmore et al. | 600/456 |
| 5,062,427 A | 11/1991 | Seo et al. | |
| 5,390,677 A | 2/1995 | Ferrera et al. | |

FOREIGN PATENT DOCUMENTS

| | | |
|---|---|---|
| WO | WO 00/51495 A1 | 8/2000 |

* cited by examiner

*Primary Examiner*—Marvin M. Lateef
*Assistant Examiner*—Ruby Jain
(74) *Attorney, Agent, or Firm*—Wolf, Greenfield & Sacks, P.C.

(57) ABSTRACT

Techniques are provided for obtaining selected instantaneous area measurements for a dynamic orifice through which blood is flowing in at least one direction, for obtaining instantaneous flow rates of blood passing through such a dynamic orifice and for obtaining flow volume for blood passing through a dynamic orifice. All of these techniques involve ensonifying a thin sample volume of blood flow exiting at the orifice, which volume is in a region of flow which is substantially laminar, such region normally being the vena contracta for the orifice, with an ultrasonic pulsed Doppler signal, receiving backscattered signal from blood within the sample volume and forming a power-velocity spectrum from the received backscattered signal. Techniques are disclosed for assuring that only laminar flow is looked at in forming the power-velocity spectrum. To obtain instantaneous area measurements, the power integral of laminar flow from the spectrum is formed, this power integral being proportional to an instantaneous cross-sectional area of the orifice. For instantaneous flow rates, the instantaneous power-velocity integral is formed from the laminar flow of the spectrum, while flow volume is obtained from the timed integral of the instantaneous flow rate.

89 Claims, 16 Drawing Sheets

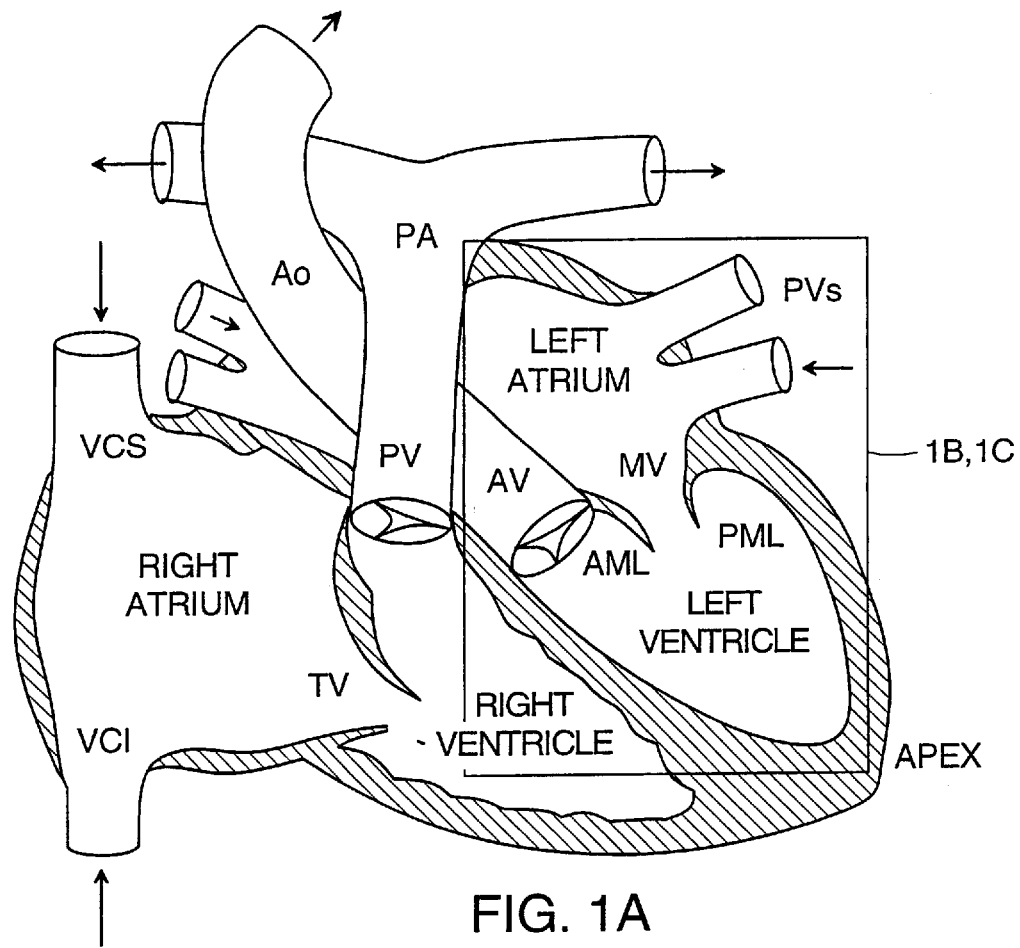
FIG. 1A
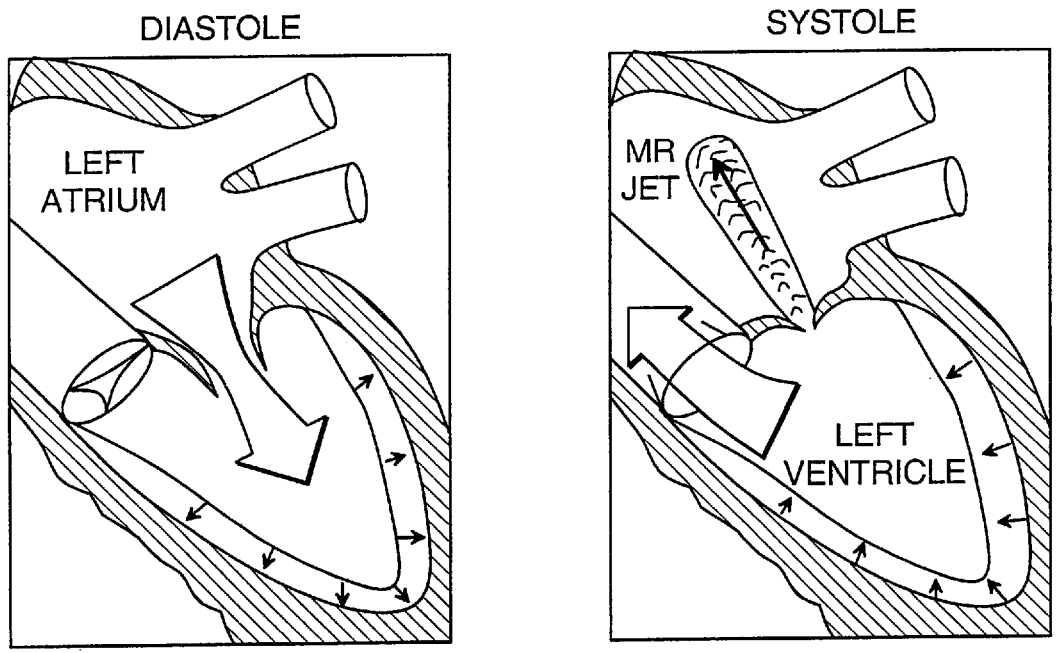
FIG. 1B
FIG. 1C

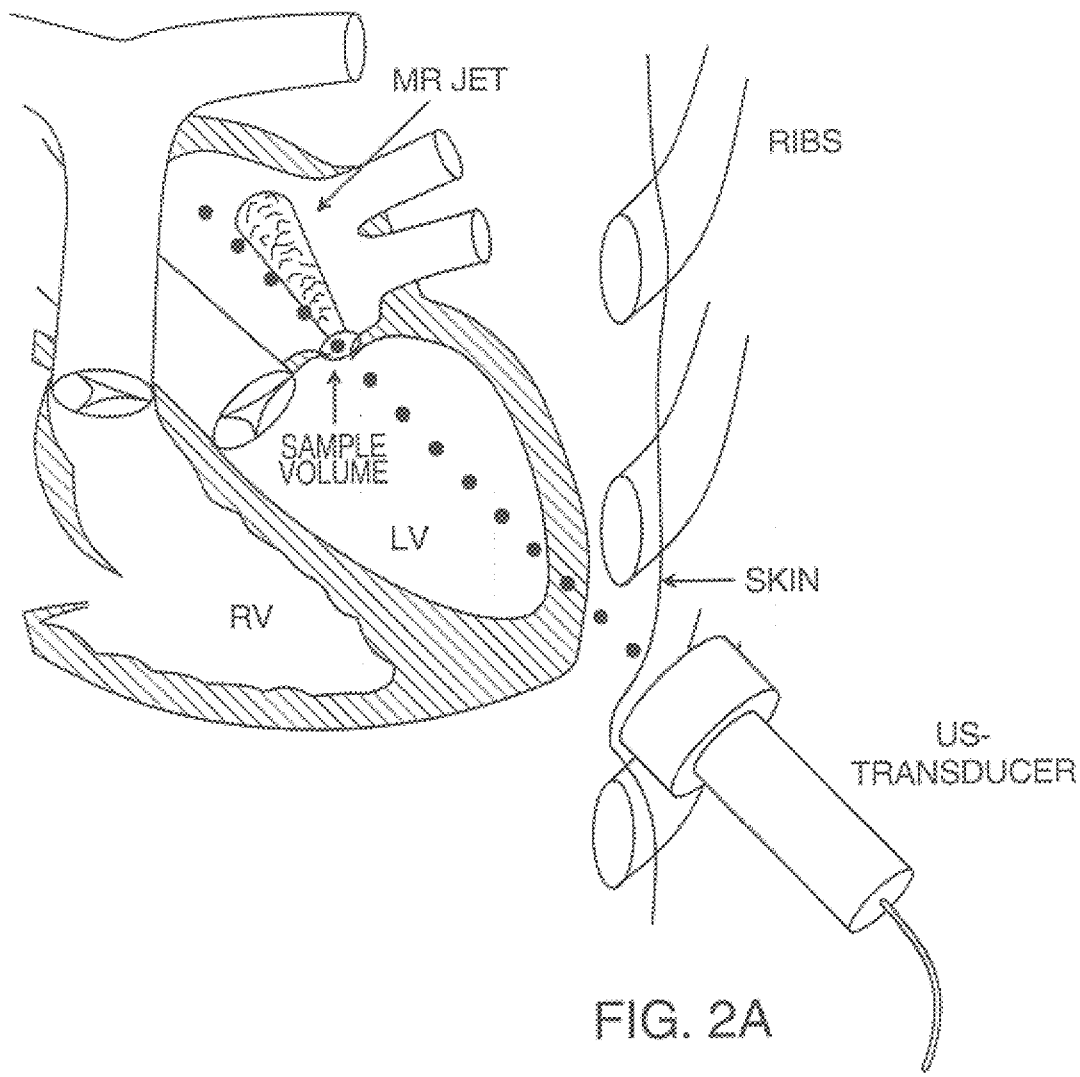
FIG. 2A
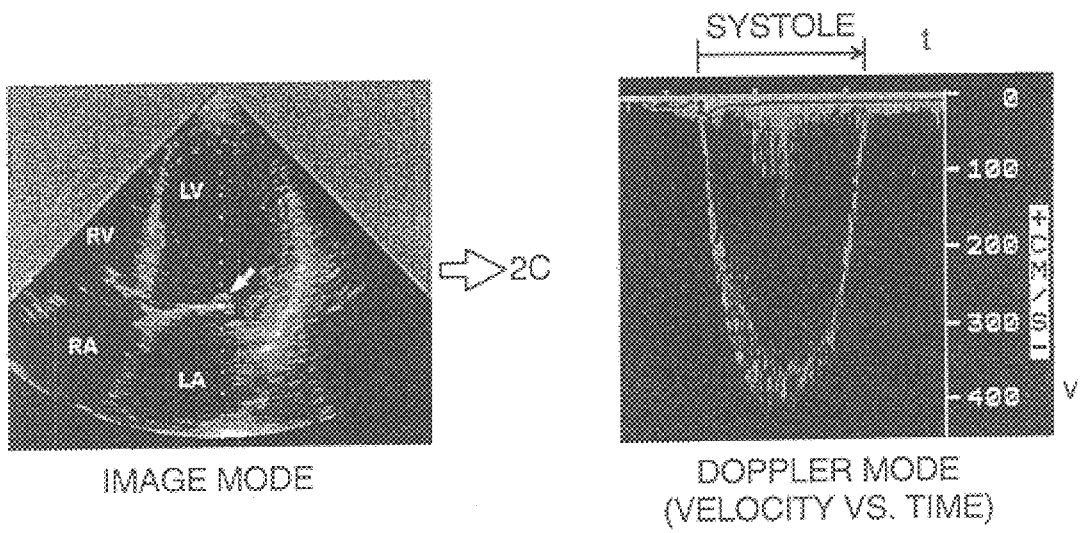
IMAGE MODE
FIG. 2B
DOPPLER MODE
(VELOCITY VS. TIME)
FIG. 2C

IN VITRO STEADY FLOW

IN VIVO PARABOLIC FLOW $$\dot{Q}_V(t) = \int_{A_l} \delta\dot{Q}(x,y,t)$$

$$\delta\dot{Q}(x,y,t) = \vec{v}_2(x,y,t) \cdot \delta\vec{A}(x,y)$$

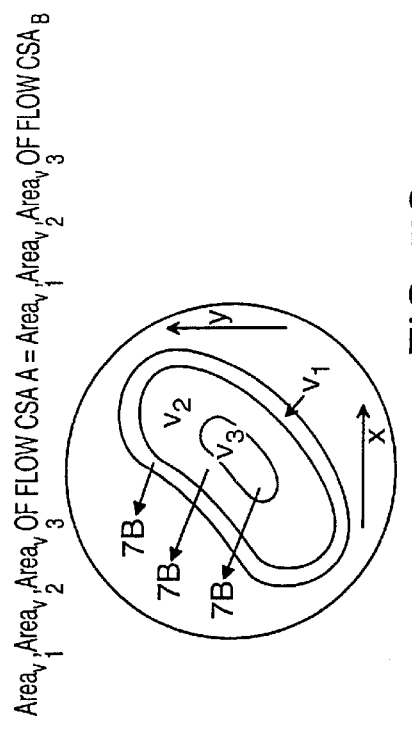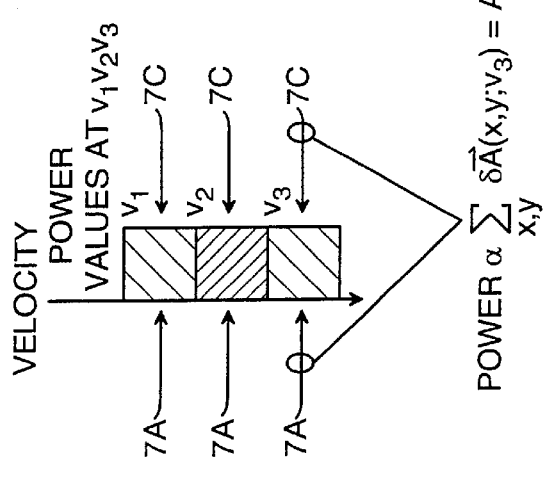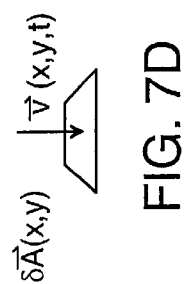

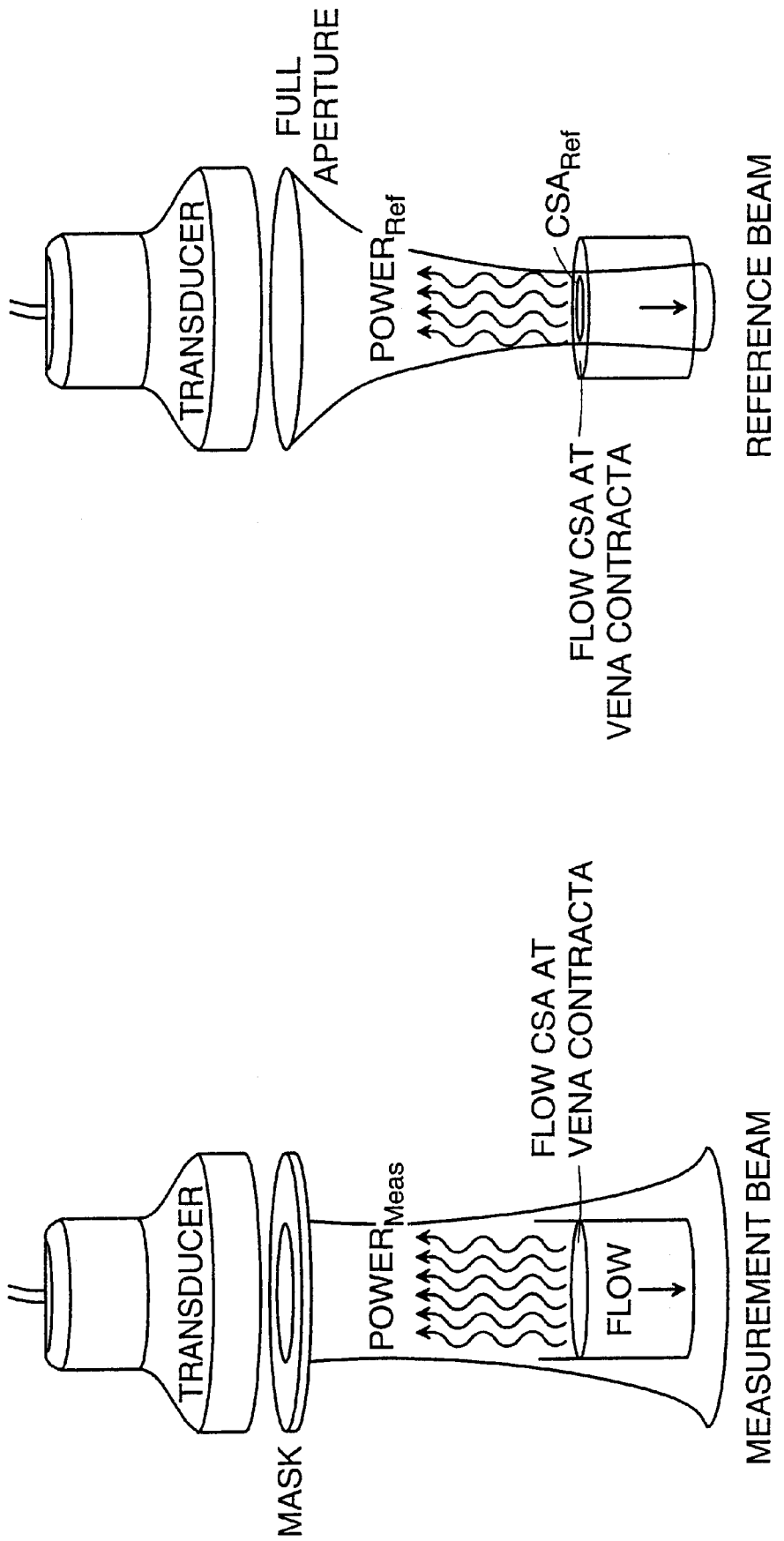

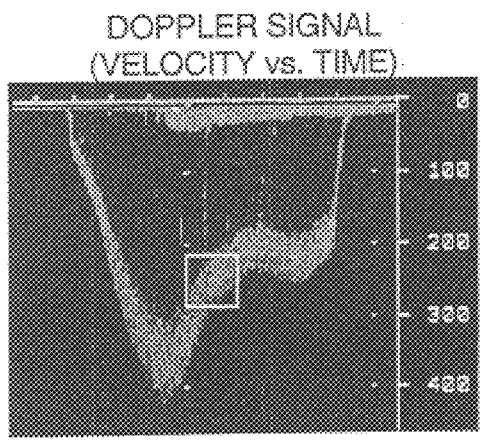
FIG. 9A
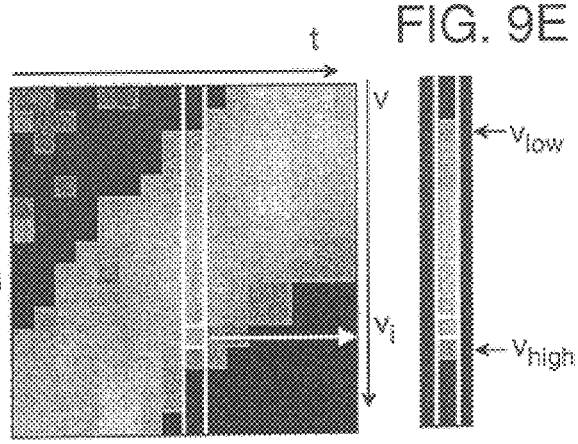
FIG. 9B
FIG. 9E
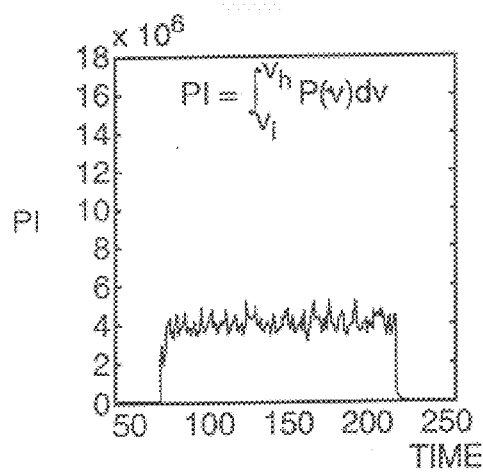
FIG. 9C
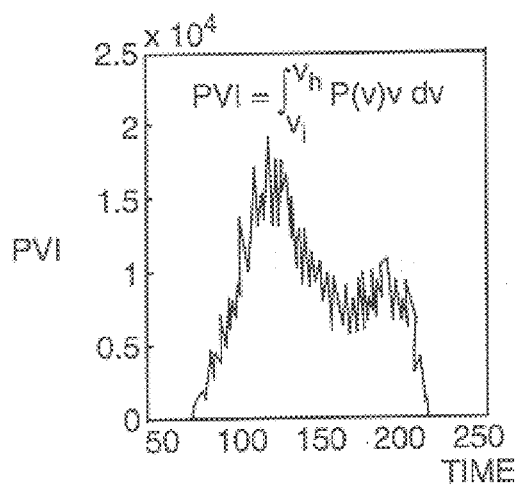
FIG. 9D

METHOD AND APPARATUS FOR MEASURING VOLUME FLOW AND AREA FOR A DYNAMIC ORIFICE

RELATED APPLICATION

This application claims priority from provisional application Serial No. 60/122,926, filed Mar. 5, 1999, the contents of which are incorporated herein by reference.

GOVERNMENT RIGHTS

Work in this invention was supported in part by Grants HL38176 and HL57302 from the National Institute of Health, Bethesda, Md. and BU 1097/-1 from the Deutsche Forschungsgemeinschaft, Bonn, Germany.

FIELD OF THE INVENTION

This invention relates to methods and apparatus for utilizing an ultrasonic pulsed wave Doppler signal to measure the instantaneous area of a dynamic orifice through which blood is passing and/or to measure instantaneous flow rate and flow volume of blood passing through such a dynamic orifice, and more particularly to such methods and apparatus which involves ensonifying a sample volume of blood flow exiting the orifice and identifying the region of such flow which is substantially laminar.

BACKGROUND OF THE INVENTION

Ultrasound, and more specifically the frequency range from 1 MHz to 5 MHz, is used for real-time imaging of the beating heart. In the human heart, the efficiency of getting blood pumped through the body is dependent on a series of four one-way valves, each separating the two contracting chambers of the heart, which valves are prone to a variety of diseases, often times resulting in their inability to close properly. Ultrasound, through the use of the Doppler concept, is able to obtain information pertaining to blood flow within the heart and in the vicinity of the valves for diagnostic purposes, ultrasound having become the most important noninvasive diagnostic technique for cardiovascular disease. However, the use of noninvasive ultrasound techniques to quantify pathologic backflow associated with valvular heart disease, other cardiac pathologies such as inter-septal shunting and other blood flows through dynamic orifices of unknown area has been an elusive medical goal for many years.

While for the purpose of this discussion, focus will be on valvular regurgitation, that is the pathologic backflow of blood through a one-way valve when in the closed state, which is a serious, and at times life-threatening, condition common in virtually all acquired and congenital heart disease, the invention is by no means limited to this application, and some other applications will be discussed later.

Leakage of one or more valves is caused by various diseases which prevent the leaflets of the valve from closing sufficiently, thereby creating a lesion called a regurgitant orifice. There is a need to accurately measure the volume of regurgitation (reverse blood flow) as a guide both to diagnosis and to therapy, especially now that valve repair techniques allow interventions to be considered earlier in the disease before dilation of the chambers (atria and ventricles) and subsequent heart failure occur. Current uncertainties regarding the natural history of the valve disease and the optimal timing of surgery are compounded by a limited ability to measure the basic lesion. Noninvasive procedures for quantification of regurgitant volume based on ultrasound do exist, but are subject to limitations that include: inaccurate diagnosis of lesion severity resulting from indirect measurements, multiple step procedures prone to error, and limiting assumptions about the flow associated with the lesion. In fact, there is currently no truly satisfactory method for noninvasive quantification, and even routine invasive methods, being costly and potentially risky, are only semi-quantitative. Those invasive methods are based on direct catheterization of the heart that allows obtaining information about flow, volume, pressure, etc.

The fundamental problem in using noninvasive ultrasound is that Doppler measures the velocity, not the desired volume, of regurgitant blood flow. Therefore, in order to determine volume of blood passing through an orifice, for example the regurgitant orifice of a diseased heart valve, the area of flow, also referred to as the effective orifice area, has to be known. All methods to date have failed to measure the effective orifice area accurately because of the complex shape and dynamic changes of this area throughout the period of flow.

A potential solution is to use the backscattered acoustic power measurements of the received spectral Doppler signal as a measure of the area of flow. It is well known that each frequency component of the Doppler spectrum provides a measurement of acoustic power that is proportional to the volume of scatterers moving through the Doppler ultrasound beam at the velocity corresponding to the Doppler frequency. It follows that velocity times power, integrated over the entire velocity spectrum, should then be proportional to the volume flow rate Q• of all scatterers (mainly red blood cells) passing through the ultrasound beam, since the blood volume is related to the concentration of red blood cells by way of the hematocrit.

This Doppler power principle holds only for laminar flow and was applied to flow in vessels but it has long been assumed that it cannot be applied to regurgitant jets, that is jets comprised of the regurgitant flow of blood, since the assumption is that the jet contains turbulent eddies which are believed to increase the backscattered power. In addition, entrainment of blood into the jet can contribute to the overestimation of the actual flow through the orifice.

While the problems of measuring flow volume and/or orifice area for a dynamic orifice through which blood flows is a particular problem when measuring regurgitant flow through a heart valve, similar problems arise in measuring valvular stenosis, septal defects with shunt flow, and peripheral vascular disease with vessel obstruction. In these and other applications, a need exists for an improved noninvasive method and apparatus for measuring flow volume and/or orifice area for a dynamic orifice having blood flow therethrough, which technique does not suffer the limitations discussed above for existing methodologies.

SUMMARY OF THE INVENTION

In accordance with the above, a method and apparatus are provided for obtaining instantaneous area measurements for a dynamic orifice through which blood is flowing in at least one direction. The technique involves ensonifying a thin sample volume of blood flow exiting the orifice, which volume is in a region of flow which is substantially laminar, with an ultrasonic pulsed Doppler signal; receiving backscattered signal from blood within the sample volume; forming a power-velocity spectrum from the received backscattered signal; and forming the power integral of the laminar flow from the spectrum, this power integral being proportional to an instantaneous cross-sectional area of the orifice. A time profile of instantaneous areas of flow for the orifice may be obtained by repetitively performing the laminar flow power integral measurement for successive time intervals. The portion of laminar flow in the power velocity spectrum is preferably determined. For preferred embodiments, the sample volume is at the vena contracta of flow exiting the orifice. The vena contracta is the smallest cross-sectional area traversed by flow just beyond the orifice, it being found that flow is substantially laminar at the vena contracta, this vena contracta being the region where entrainment of flow turbulence is at its minimum. For preferred embodiments, the ultrasonic Doppler signal is electronically steered and focused to the vena contracta and is preferably wide enough so as to fully ensonify the vena contracts. The electronic steering and focusing may be performed by moving the ultrasound signal through blood flow exiting the orifice, and detecting a Doppler spectral display and/or audio output, the signal being at the vena contracta when the Doppler signal consists primarily of laminar flow. To assure that only signal from laminar flow is utilized in performing the power integral calculation, the power velocity spectrum is preferably smoothed to eliminate the effects of any aberrations therein, and the velocity for peak power is determined for each time interval. A lower velocity of laminar flow is then determined as being a selected velocity, for example the maximum velocity, which is less than the velocity at peak power where the power is at a selected percentage of the peak power, and an upper velocity of laminar flow is determined which is a selected velocity, for example a minimum velocity, greater than the velocity at peak power where the power has dropped to a specified percentage of the peak power. Depending on application, the percentage of peak power may be from approximately 30% to approximately 60%, with approximately 50% or −3 db being the percentage of peak power for an illustrative embodiment. Only the power-velocity spectrum between the lower velocity and upper velocity, which is assumed to be derived from flow which is substantially laminar, is utilized in doing the power integral calculation, thus assuring that various values determined utilizing the teachings of this invention are obtained only from readings of laminar flow. The flow may for example be regurgitant flow through a faulty heart valve, the orifice area being that of lesions in the heart valve permitting the regurgitant flow.

The technique may also include calibrating to permit absolute flow area to be obtained. Calibrating may include applying a narrow ultrasound reference beam placed within the laminar flow in the vena contracts, the reference beam having a known cross-sectional area ($CSA_{ref}$), and computing flow cross-sectional area ($CSA_{flow}$) from $CSA_{flow}=CSA_{ref} \cdot PI_{meas}/PI_{ref}$, where $PI_{meas}$ and $PI_{ref}$ equal the power measure by a broad measurement beam encompassing the vena contracta and the power measure by the narrow reference beam of known cross-sectional area, respectively. Where the flow being measured is regurgitant flow through a faulty heart valve, calibration may be performed by detecting backscattered Doppler ultrasound power from the reference beam for forward flow when the valve is open.

The invention also involves a technique for obtaining instantaneous flow rates of blood passing through a dynamic orifice in at least one direction, which technique includes ensonifying a thin volume of blood flow exiting the orifice, which volume is in a region of flow which is substantially laminar, with an ultrasonic pulsed wave Doppler signal which fully encompasses the cross-sectional area of the volume where flow is substantially laminar; receiving backscattered signal from blood within the pulsed wave Doppler sample volume; forming a power-velocity spectrum from received backscattered signal; and forming the instantaneous power-velocity integral (PVI) from the laminar flow of the spectrum. A pulsed wave Doppler signal, such as high-PRF Doppler, capable of representing the full range of velocity, is preferred. A time profile of instantaneous flow rates for the orifice may be obtained by calculating the instantaneous power-velocity integrals for successive time intervals. As for the flow area determination, the thin sample volume is preferably at the vena contracta of the flow exiting the orifice, with electronic steering preferably being performed on the ultrasonic signal to steer and focus it to the vena contracta and is wide enough so as to fully ensonify the vena contracts. The electronic steering and focusing may be performed by scanning the ultrasound signal through blood flow exiting the orifice and detecting at least one of Doppler spectral display and audio output, the signal being at the vena contracta when the output of the detecting step identifies laminar flow. Flow at non-laminar velocities may be eliminated from the PVI determination in the manner described above. The flow may for example be regurgitant flow through a faulty heart valve, the orifice area being that of lesions in the heart valve permitting regurgitant flow.

Calibration may also be performed to permit absolute flow rate to be obtained, calibration including applying a narrow ultrasound reference beam placed within the laminar flow in the vena contracta, the reference beam having a known CSA ($CSA_{ref}$), and computing Flow rate from Flow rate=$CSA_{ref} \cdot PVI_{meas}/PI_{ref}$. Where the flow being measured is regurgitant flow through a faulty heart valve, calibration may include detecting backscattered Doppler ultrasound power from the reference beam when the valve is open for forward flow.

Finally, the invention involves a technique for obtaining flow volume for blood passing through a dynamic orifice in at least one direction, which technique includes ensonifying a thin volume of blood flow exiting the orifice, which volume is in a region of flow which is substantially laminar, with an ultrasonic pulsed wave Doppler signal which fully encompasses the cross-sectional area of the volume where flow is substantially laminar; receiving backscattered signal from blood within the pulsed wave Doppler sample volume; forming a power-velocity spectrum from received backscattered signal; and forming the instantaneous power-velocity integral (PVI) from the laminar flow portion of the spectrum and the profile of the instantaneous flow rates. The flow volume is obtained from the time integral of the instantaneous flow rate (PVTI). As for prior embodiments, a pulsed wave Doppler signal, such as high-PRF Doppler, is preferred, the thin sample volume is preferably at the vena contracta of the flow exiting the orifice, the technique preferably includes electronic steering and focusing the ultrasonic signal to vena contracta, and non-laminar velocities being removed from the calculations using techniques previously discussed. The ultrasound signal is preferably wide enough so as to fully ensonify the vena contracta. The flow may for example be regurgitant flow through a faulty heart valve, the orifice area being that of lesions in the heart valve permitting regurgitant flow. Where the flow is regurgitant flow through a faulty heart valve, detected forward and regurgitant flow may be combined to obtain a measure of regurgitant fraction.

Calibration may also be performed to permit absolute flow volume to be obtained, calibration including applying a narrow ultrasound reference beam placed within the laminar flow in the vena contracta, the reference beam having a known CSA ($CSA_{ref}$), and computing Flow volume from Flow volume=$CSA_{ref} \cdot PVTI_{meas}/PI_{ref}$. Where the flow being measured is regurgitant flow through a faulty heart valve, calibration may include detecting backscattered Doppler ultrasound power from the reference beam when the valve is open for forward flow.

The foregoing and other objects, features and advantages of the invention will be apparent from the following more particular description of preferred embodiments of the invention as illustrated in the accompanying drawings.

IN THE DRAWINGS

FIG. 1A is a representation of the anatomy and physiology of the human heart, FIG. 1B and FIG. 1C being enlarged views for a portion of the heart shown in FIG. 1A during diastolic and systolic phases, respectively;

FIG. 2A is an illustration of data acquisition using an ultrasonic transducer in accordance with the teachings of this invention;

FIG. 2B is an ultrasonic display for two-dimensional image mode, and FIG. 2C is an exemplary ultrasonic display at the vena contracta for Doppler mode;

FIG. 7 is a diagram illustrating the independence of the power-velocity spectrum from the distribution of velocities across the flow CSA;

FIG. 8 is a diagrammatic representation illustrating calibration using a broad measurement beam and a narrow reference beam;

FIGS. 9A–9D are a high-PRF Doppler signal, an enlarged sector of the signal shown in FIG. 9A, a PI plot and a PVI plot, respectively for an exemplary orifice and flow profile;

DETAILED DESCRIPTION

Referring first to FIG. 1A, the heart is shown as having four chambers—left and right ventricle (LV and RV) and left and right atrium (LA and RA). These chambers are connected by four one-way valves, the mitral (MV), aortic (AV), tricuspid (TV) and pulmonary (PV) valves. There are also various vessels going in and out of the heart. The arrows in FIG. 1A indicate the direction of the blood where the venous return enters the right heart via the right atrium and is pumped by the right ventricle via pulmonary valve and pulmonary artery to the left and right lung. After oxygenation in the lungs, the blood re-enters the heart via the pulmonary veins and flows to the left ventricle via the left atrium and the mitral valve. The left ventricle, as the strongest contracting chamber, pumps the oxygenated blood to the entire body via the aortic valve and the aorta, thereby creating the systemic blood pressure.

FIGS. 1B and 1C indicate the direction of blood flow during the two phases of one heart cycle, diastole where the left ventricle relaxes to refill with blood from the left atrium, and systole where the left ventricle contracts to eject the blood to the aorta. FIG. 1C shows the pathologic regurgitant flow when the mitral valve closes incompletely during systole.

FIG. 2A illustrates the use of an ultrasonic transducer to acquire data on the heart. The ultrasonic transducer is positioned onto the outer chest wall of the patient, and its beam is oriented to the region of flow. A high-PRF Doppler sample volume is depicted, which is located in the vena contracta which, as indicated previously, is the narrowest portion of the jet. FIG. 2B shows how a two-dimensional image plane intersecting the heart is used to navigate the Doppler beam so as to place the sample volume at the vena contracts, which is at the white arrow in FIG. 2B. Once the beam is located, the system may be changed to pulsed Doppler mode to register the Doppler signal as depicted in FIG. 2C. The velocities are displayed below a baseline of 0, indicating that the flow is away from the transducer passing from the left ventricle through the diseased mitral valve back to the left atrium.

Figure 3B:
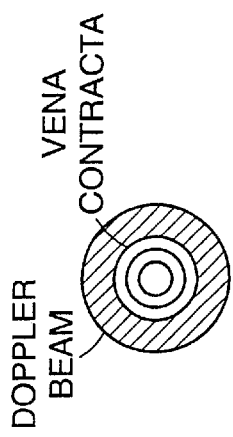
FIG. 3 is a representation of the anatomy for a regurgitant jet.
Figure 3C:
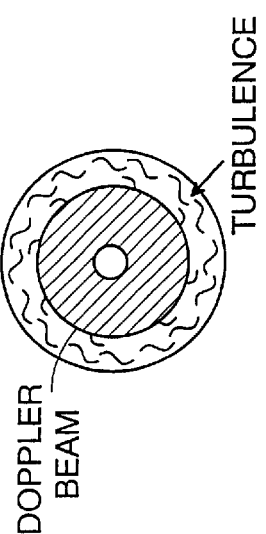
Figure 3A:
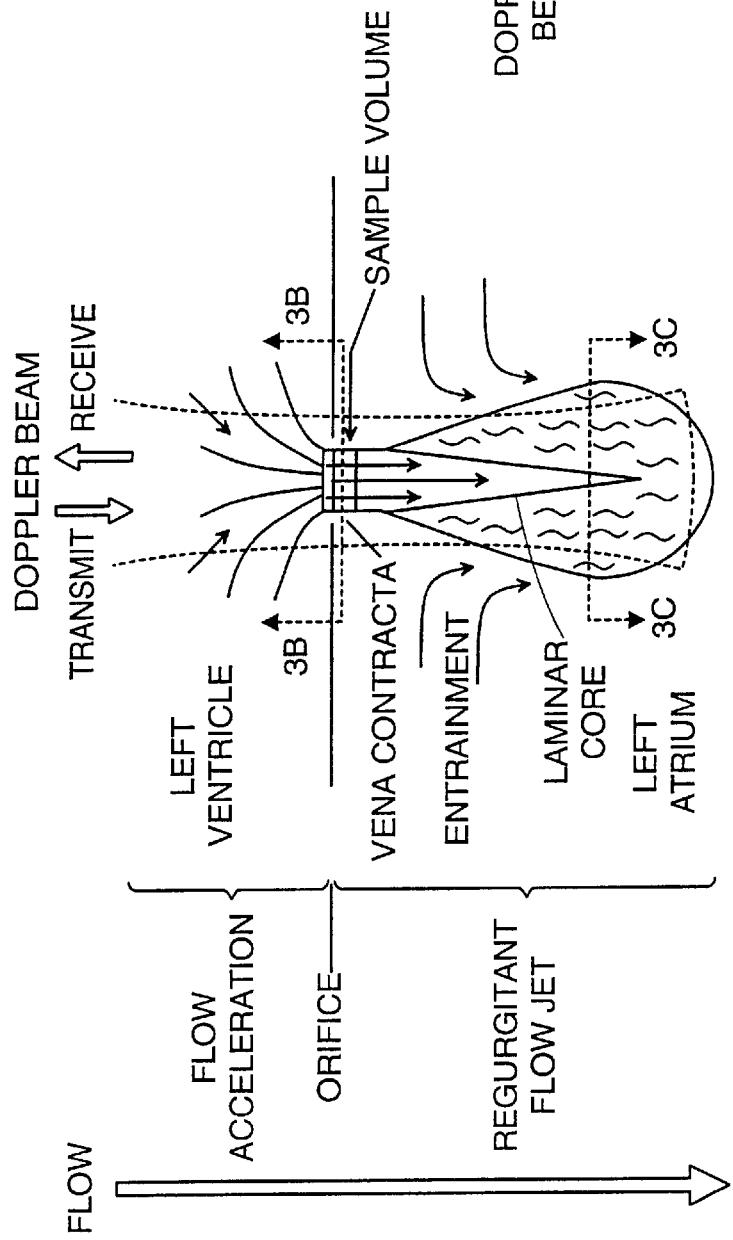

FIG. 3 is a diagram illustrating the anatomy of a regurgitant jet, illustrating the vena contracta, the core of laminar flow, and the regions of entrainment of fluid and turbulence. The vena contracta is shown as the narrowest portion of the regurgitant jet just below the orifice where velocities are highest and flow is laminar across the jet prior to entrainment of fluid and turbulence. The figure also indicates the Doppler beam and the sample volume located at the vena contracta. Cross-sectional views at the right indicate the laminar flow at the vena contracta and the turbulent flow beyond the vena contracta.

Basic Principles

Figure 4A:
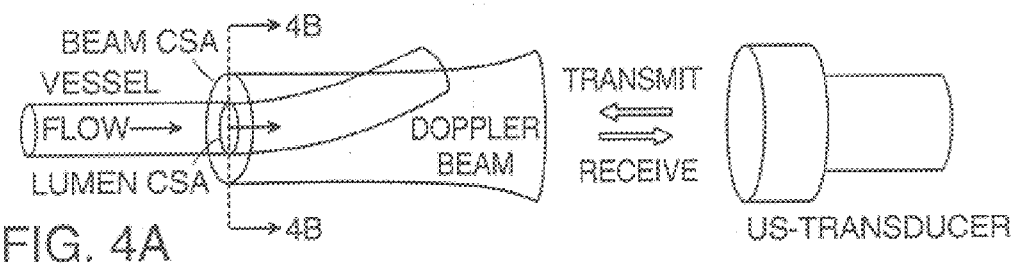
FIG. 4A is a diagrammatic representation of the sonification of an area of flow by a Doppler beam for a Doppler angle θ=0.
Figure 4B:
FIG. 4B is a diagrammatic representation of an exemplary velocity distribution across an area of flow.

Referring to FIG. 4A, for Doppler operation, the ultrasound system, through the use of a hand-held transducer, transmits an ultrasound beam that is electronically steered and focused. It is the backscattered ultrasound that provides the diagnostic information, the ultrasound energy within the beam backscattered as it propagates within the body. To acquire the backscattered signal, the ultrasound system operates in 'reverse' using the same transducer to receive the backscattered energy, again with electronic steering and focusing.

Figure 4C:
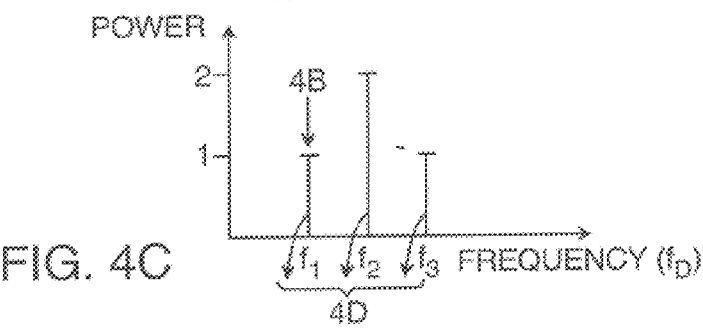
FIG. 4C is a plot of backscattered power versus frequency from the received Doppler spectrum shown in FIG. 4B
Figure 4D:
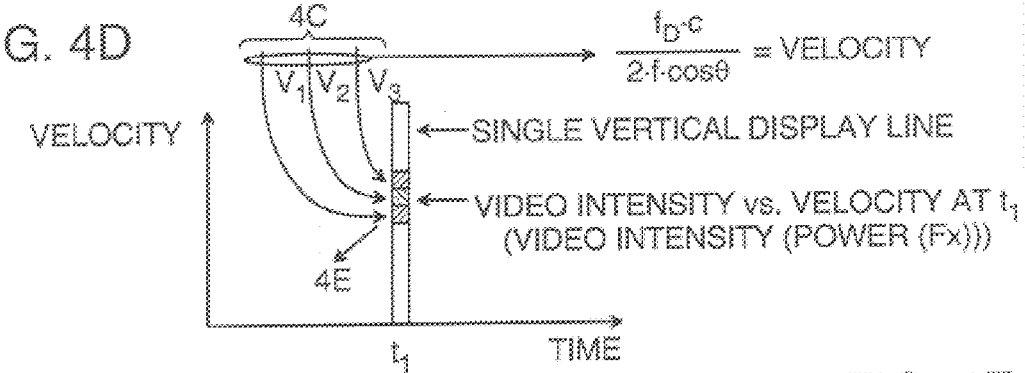
FIG. 4D is a plot illustrating the conversion of power and frequency to display video intensity and velocity.
Figure 4E:
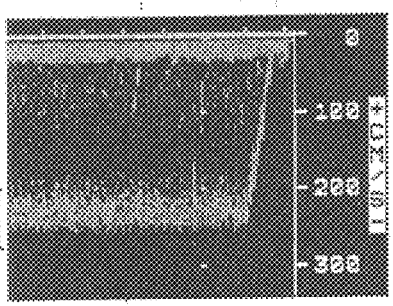
FIGS. 4E and 4F are exemplary displays of actual flow measurements (velocity vs. time) by Doppler for in vitro steady flow and in vivo parabolic flow, respectively.
Figure 4F:
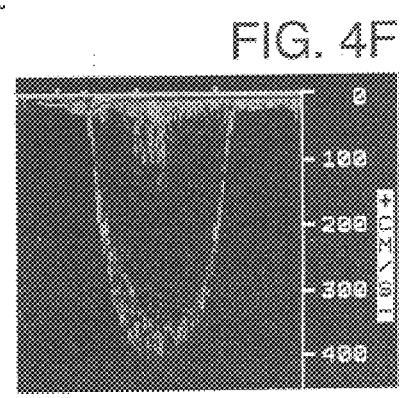

The spectral Doppler power is proportional to the volume of backscatterers on a frequency basis. This power spectrum is mapped to a vertical line of display intensity. The spectrum is computed and displayed continually and in real-time as depicted in FIGS. 4E and 4F. Parabolic flow (FIG. 4F) pertains to the shape of the narrow-band velocity trace over time from an in vivo pulsatile flow through a mitral valve regurgitant orifice during systolic left ventricular contraction in a patient. For FIG. 4C, power at f2 is twice as large as at f1 or f3 because the area of V2 is twice as large as of V1 and V3.

In the Doppler modality of operation, the power spectrum of the demodulated received waveform is computed using an FFT algorithm and analyzed by the ultrasound imaging system. The analysis of the received Doppler signal provides two important components; the Doppler frequency and the corresponding backscattered signal strength (acoustic power).

The velocity of the backscattering medium, presumably blood within a sample volume at the focal region, is related to the frequency of the power spectrum of the backscattered ultrasound by the equation, $$f_D = 2\frac{f}{c}|V_{SC}|\cos\theta \qquad (1)$$

where $f_D$ denotes the Doppler frequency of the backscattered signal, f denotes the transmit frequency of the ultrasound, c denotes the speed of propagation of sound within the medium, (the approximate speed of sound in water is 1470 m/sec, in soft tissue 1540 m/sec and in bone 4800 m/sec), $V_{SC}$ denotes the velocity of the scattering object, presumably blood, and $\theta$ denotes the angle between the direction of the ultrasound beam and the direction of blood velocity. A derivation of Eq. 1 based on the amplitude/phase data of the demodulated received signal rather than the basic Doppler concept is provided in Appendix A.

Using "somewhat conventional" procedures, for example the use of the fast Fourier transform (FFT), the spectral content of the backscattered Doppler signal is determined. The spectral bins of sufficient amplitude not only indicate blood flow at velocities as determined by Eq. 1, but also backscattered power is proportional to the amount of blood flowing at the corresponding velocity (FIG. 4C). However, in the present systems, where the Doppler spectrum of blood flow is generated and displayed in real-time, only the velocities are interpreted for diagnostic purposes.

Figure 5A:
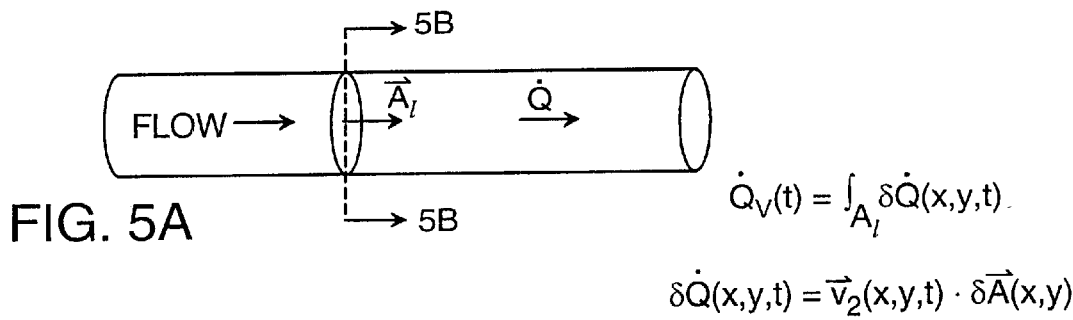
FIG. 5 is a diagrammatic illustration of the principle of volume flow rate calculation over an area of flow for a spectrum of three different flow velocities.
Figure 5B:
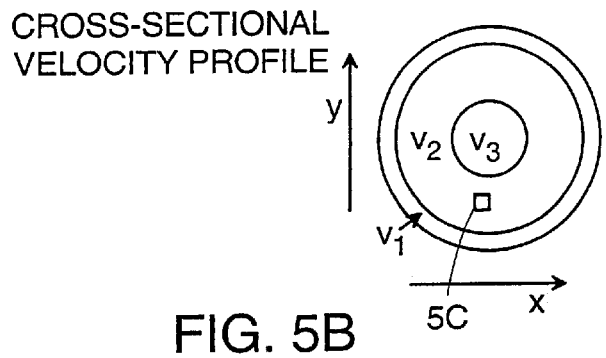
Figure 5C:
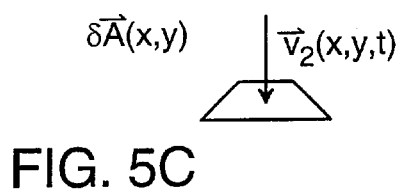

The basic concept for using the Doppler spectral information to quantitate flow rate and volume is as follows:

First, referring to FIG. 5, for the purpose of concept presentation a lumen is defined, as a bounded cross-sectional planar area denoted by the vector $A_1\rightarrow$ of direction perpendicular to the planar surface, through which flows an incompressible fluid with directional velocity function $v\rightarrow(x, y, t)$ across the area of flow at instantaneous time t. The incremental flow $\delta Q\bullet(x, y, t)$ passing through the differential area $\delta A\rightarrow(x, y)$ at time t is given by $v\rightarrow(x, y, t)\bullet\delta A\rightarrow(x, y)$ where $\bullet$ denotes the dot product operation of two direction vectors. The dot product of two vectors a and b is defined as the product of their magnitudes times the cosine of the angle between them. The total flow passing through the planar cross-sectional area encompassed by the lumen is given by the integral expression $$Q\bullet(t) = \int_{A_t} v \rightarrow (x, y, t)\bullet\delta A \rightarrow (x, y) \qquad (2)$$

The flow volume, $Q_v$, within an interval of time, for example, within the systolic portion of the cardiac cycle, can be obtained by integrating the instantaneous flow over the time interval of interest denoted T, that is, $$Q_v = \int_T Q\bullet_v(t)dt \qquad (3)$$

The uniqueness of this approach is the capability to measure the regurgitant flow rate and flow volume noninvasively and directly at the valve lesion using only the backscattered power and velocity information, both of which are contained in the received ultrasound spectrum. This is accomplished as follows: A sample volume of cross-sectional area that encompasses the area of regurgitant flow at the vena contracta is sonified with the ultrasound beam. It is important to note that the flow within the sample volume when placed at the vena contracta contains the laminar flow of the vena contracta and nonlaminar flow of the blood surrounding the vena contracta unlike in prior art where blood flow was constrained within the wall of the vessel. While the Doppler spectrum from a sample volume applied to such a vessel only contains the signal from the vessel flow, the Doppler spectrum from the sample volume of a regurgitant jet at the level of the vena contracta contains signal from laminar and turbulent flow. This requires the identification of the laminar portion of the Doppler spectrum and the use only of this portion in the calculation of the measurements.

To accomplish the above, the operator of the system initially utilizes a standard ultrasonic beam control, such as a joy stick or tracker ball, to adjust the beam as shown in FIGS. 2A and 2B to pass through the mitral valve or other valve of interest. The depth for imaging is then adjusted on the machine in standard fashion so as to be directly adjacent a regurgitant side of the valve at the vena contracta. All this is done with the ultrasound system in image mode as shown in FIG. 2B, the desired imaging spot being generally at the bright dot being pointed to by the arrow.

At this point, the beam is focused at substantially the desired point, but may not be exactly centered with the flow to be measured. To fine tune the position, the ultrasound system is switched to Doppler mode, resulting in a display such as that shown in FIG. 2C, illustrating velocity versus time. FIG. 9A is an alternative image. The bright signals in the low velocity area on these displays, for example under 100, is generally tissue noise, turbulent flow, and the like, while the bright higher frequency band on the outside of each of these images is generally from laminar flow. When in the vena contracta where laminar flow predominates, the narrowness and cleanness of this bright narrow-band spectrum will be optimized. Generally, in order to eliminate the effect of aberrations in the backscattered signal, the backscattered signal is smoothed utilizing a standard averaging or smoothing technique. The operator then looks at the Doppler mode image and fine tunes transducer position and/or image depth until the "cleanest" observed image is obtained. Alternatively, the smoothed backscattered signal may be converted to audio, the signal from the vena contracta being the cleanest tone involving the fewest frequencies. Theoretically this fine tuning could be done automatically, with for example the beam position and depth being slightly adjusted through a small range, and for example an audio signal being monitored to provide a feedback signal for controlling the beam in a direction resulting in the cleanest audio output. This could be done first for position and then for depth, or the two could be done simultaneously in accordance with a selected feedback controlled scanning algorithm.

However, as indicated above, even when the beam is positioned exactly at the vena contracta, in order for the beam to ensonify the entire vena contracta, it will inherently also ensonify some of the surrounding turbulent flow. In order to ensure that only signal from laminar flow at the vena contracta is utilized for performing the various calculations in accordance with the teachings of this invention, a velocity filtering technique may be utilized, which technique is illustrated in FIGS. 9A and 9B. Referring to FIG. 9B, which is an enlarged image of the portion of FIG. 9A shown in the rectangle, it is seen that the backscattered signal contains a number of velocities, the power at a given velocity for the time $t_i$ being indicated by the brightness of the image for the velocity $V_i$ at the given time, a brighter image indicating more power. For each time $t_i$ a determination is made of the velocity of peak power in the smoothed power-velocity spectrum for the sample $t_i$ in FIG. 9B, which is also shown at the right of the Figure. From this image, peak power is found to extend over a velocity range $V_r$, a velocity in this range being utilized as the velocity of peak power for this time interval. A determination is then made of the lower velocity of laminar flow ($V_{low}$) which is considered to be the maximum velocity which is less than the velocity for peak power (i.e., $V_R$) where the power is a specified percentage of peak power. This percentage may, for example, be in an approximate range of 30% to 60% of peak power depending on application, being 50% or −3 DB for an illustrative embodiment. Similarly $V_{high}$, the upper velocity of laminar flow is determined by finding the minimum velocity which is greater than the velocity $V_R$ of peak power where the power is the specified percentage of the peak power. While the specified percentage of peak power need not be the same for determining $V_{low}$ and $V_{high}$, these percentages are the same for an illustrative embodiment and would normally be the same. Once $V_{low}$ and $V_{high}$ are determined for a given time $t_I$, only backscattered radiation having a velocity falling within this range is utilized and performing the various calculations, thus assuring that only laminar flow at the vena contracta is being utilized for these calculations.

Pulse-wave (PW) Doppler is used since, as described in Appendix A, this allows a range gate to be set which in turn controls the thickness of the interrogated volume. In PW Doppler, a relatively short pulse is transmitted and the sample volume thickness is controlled by receiving and analyzing the backscattered ultrasound for a relatively short interval of time. The total backscattered acoustic power from such a Doppler sample volume is linearly proportional to the sonified blood volume, where the proportionality factor is given by the backscattering coefficient that is related to the number of independent scatterers, mainly red blood cells (erythrocytes), in this volume.

Figure 6:
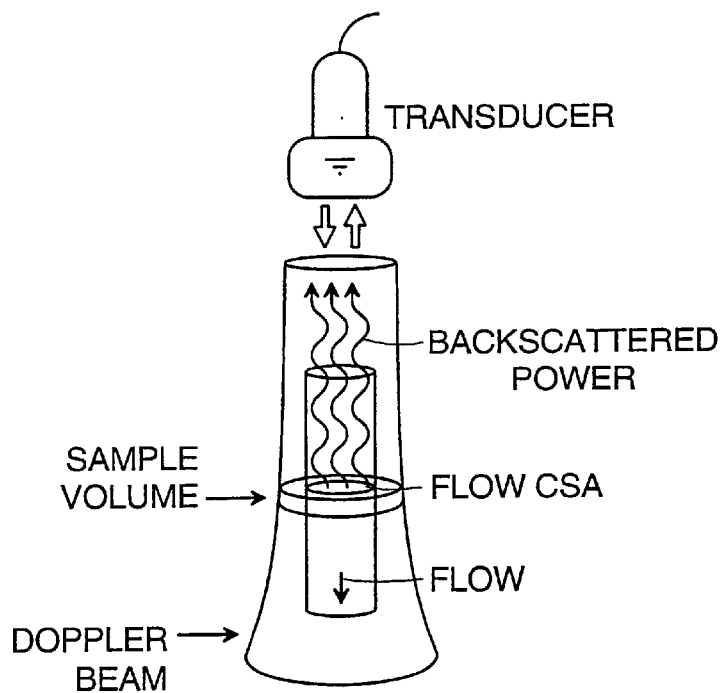
FIG. 6 is a diagrammatic representation illustrating the proportionality of backscattered Doppler power to a sonified volume of blood.

Further, if a disk-like sample volume is traversed by blood flow, then the backscattered power is linearly proportional to the cross-sectional area (CSA) of the flow within the lumen projected onto the surface of the sample volume of the sonifying ultrasound beam as shown in FIG. 6. This assumes that the thickness of the sample volume is thin and constant, that the concentration of scatterers (hematocrit) is constant, and that the beam encompasses the entire CSA of flow. For example, the total backscattered power from a jet with a CSA of 1.0 cm$^2$ would be twice as much as from a jet with a jet CSA of 0.5 cm$^2$.

This approach does not require the existence of a lumen nor the explicit determination of the velocity distribution over the cross-sectional area of the vena contracta. Rather, the Doppler beam encompassing the entire area of flow, effectively integrates the contribution of all scatterers at each velocity of laminar flow regardless of the velocity profile (FIG. 7). That is, in the Doppler modality the backscattered acoustic signal power increases linearly by the number of scatterers traveling at the same velocity, independent of their individual locations within the jet CSA and independent of their individual locations within the sample volume. As a consequence, it becomes clear that with this application of the Doppler beam analyzing the backscattered power-velocity spectra, there are no longer concerns about the velocity distribution of scatterers across the flow CSA or about the shape and area of the flow CSA (FIG. 7), assuming a uniform sensitivity across the transmit and receive beam CSA. Thus, in FIG. 7, the areas of V1, V2, and V3 in flows A and B having the same size but different shapes are represented by the same power spectrum.

In order to detect the weak backscattered signal from blood, the Doppler modality requires the elimination of signal backscattered from tissue prior to the calculation of the power spectrum, since the backscattered power of tissue can be 100 to 1000 times greater than the power backscattered by blood. This is done by a high-pass filtering process, referred to as a wall filter, that eliminates Doppler signals backscattered from low velocity targets such as tissue. Hence even though the backscattered power is independent of velocity, only the backscattered power of blood flow above the cutoff velocity of the wall filter is measured. From this it also becomes clear that blood within the sample volume that is not flowing, such as that external to the vena contracta, does not contribute to the power spectrum and therefore does not contribute to the area and associated flow measurement.

In summary, for a sample volume of uniform thickness, achieved with PW Doppler and placed in the vena contracta, the spectral Doppler power associated with a Doppler frequency, denoted P(v), is linearly proportional to the cross-sectional area of scatterers traveling at the velocity v, corresponding to the Doppler frequency. Hence, the total spectral power is linearly proportional to the cross-sectional area of the vena contracta. That is $$\text{Power} = \int_{vel} P(v) dv \propto CSA_{jet} \qquad (4)$$

This is demonstrated in the results that are contained herein.

Furthermore, the power associated with a given frequency (or velocity) times the velocity is equivalent to the area times the velocity, which in turn provides a measure of the component of flow attributable to scatterers of the specified velocity. If this calculation of power times velocity is integrated for each component of the Doppler spectrum, an estimate proportional to the total instantaneous flow passing through the vena contracta, denoted $Q\bullet_v(t)$, can be obtained. That is, $$Q\bullet(t) \propto \int_{vel} P(v) v dv \qquad (5)$$

The flow volume can be obtained from the estimates of instantaneous flow by integrating over the time interval of interest denoted T. That is, $$Q_v = \int_T Q\bullet d(t) \qquad (6)$$

These relationships are demonstrated in both in vitro and in viva experiments to be discussed later.

From this discussion, it is seen that the Doppler power-velocity principle also indicates that the backscattered power integrated over the velocity spectrum at the vena contracta is proportional to the cross-sectional area of the vena contracta, regardless of flow rate. Of note is that the proportionality between power and CSA depends mainly on attenuation and the backscattering coefficient, which is a nonlinear function of hematocrit. The calibration technique described later, however, takes this into account by comparing measured power over the entire sample volume with that in a small reference beam of known CSA.

Finally, although there is a dependence of the velocity measurement on the angle θ between the direction of flow in the vena contracta and the main axis of the Doppler beam as indicated in Eq. 1, the measurement of power times velocity is independent of this angle. That is, the Doppler velocity is decreased by the cos θ and the power measurement, being proportional to the CSA of flow projected onto the surface of the sample volume, is increased by 1/cos θ, such that $$\text{Flow rate} = (v\bullet\cos\theta)\bullet\left(\frac{Flow\,CSA}{\cos\theta}\right) \qquad (7)$$

This angle independence becomes relevant in in vivo studies where the Doppler beam cannot always be aligned with the direction of flow.

In the following section, evidence is discussed establishing that the regurgitant flow volume can be estimated/quantified using only the power and velocity information acquired with Doppler ultrasound, the discussion including both methodology of the conducted experiments and the results.

Methodology

Procedures required in practicing the teaching of this invention included: 1) generation of a Doppler beam sufficiently wide to encompass the cross-sectional area of the vena contracta of a regurgitant jet, and 2) a method of calibration to compensate for variations in attenuation and the backscattering coefficient. The following is a brief description of each procedure:

Doppler Beam-Width

For an illustrative embodiment, the full 1.2 cm by 2.0 cm transducer aperture of the transducer used produces a beam having a cross-sectional area of approximately 3.1 mm in elevation by 5.2 mm in the lateral dimension at a 10 cm depth, based on defining the border of the beam CSA by where the sensitivity of the transducer drops to the half-maximal power or −3 db. To ensonify larger flow areas, a broader measurement was produced based on the principle that the smaller the transducer aperture, the broader the distal beam (see FIG. 8). The aperture for the left measurement beam was diminished with the application of a Tyvek (Dupont) mask over the transducer face. In vitro, a 7-mm diameter circular aperture was applied, thereby increasing the half-maximum-power beam-width at a 10-cm depth to approximately 6.75 mm (CSA=0.36 cm$^2$; Appendix B). However, it was necessary to use a 10-mm aperture creating a beam-width of 5.8 cm (CSA=0.26 cm$^2$) at 10 cm for the in vivo experiments to minimize the loss of transmit power and Doppler receive sensitivity resulting from decreasing the size of the transducer aperture without compensating for the decrease of transmit power. Alternative beam broadening techniques are discussed in Appendix D.

Calibration of Doppler Power Measurements

Although the invention only requires that a proportionality exist between PVI and flow, it is necessary to calibrate the system in order to obtain absolute measurements of area and flow rate in a clinically useful manner. That is, in part because the power measurements obtained by the ultrasound system are unitless, and in part because for the same blood volume, Doppler power measurements will vary among patients due to differences in attenuation and backscattering coefficients (related to patient hematocrit). The Doppler measurements in each individual can be calibrated with a narrow reference beam that fits within an area of flow in the vicinity of the vena contracta (right beam FIG. 8). This beam is used to establish the ratio between reference power integral PI$_{ref}$ and the known CSA of the reference beam at that depth, CSA$_{ref}$. The same ratio can be applied to the power measured by the broader measurement beam, PI$_{meas}$, in order to determine the CSA of flow within the beam, provided the measurement beam encompasses the entire cross-sectional area of the vena contracts. That is $$\frac{PI_{meas}}{Flow\,CSA} = \frac{PI_{ref}}{CSA_{ref}} \qquad (8)$$

For example, if the power is four times as great as that returning from the reference signal (the narrow beam obtained with the full transducer aperture), the flow CSA at the vena contracta is four times the known CSA of the reference beam. Since the area of the reference beam is known, the calibrated power measurement provides an estimate of the flow CSA at the vena contracta.

For the illustrative embodiment, the technique used to widen the beam also reduced the transmit power and receive sensitivity due to the reduced aperture size. That is, the power measured by the broader beam is less than that of the reference beam for the same cross-sectional area of flow, assuming the cross-sectional area of flow is contained within both the narrow reference and broader measurement beam (Appendix B). Hence, there is also the need to correct for the reduction in transmit power and receive sensitivity simply resulting from the reduction in the aperture of the transducer. The relationship of the ratios of power to cross-sectional area for this condition is, $$\frac{CF \cdot PI_{ref}}{Flow\,CSA} = \frac{PI_{ref}}{CSA_{ref}} \quad (9)$$

where CF denotes the correction factor accounting for aperture reduction. This correction factor was determined in vitro by comparing the backscattered power for both beams for flow through an orifice smaller in cross-sectional area than both beam-widths (0.07 cm$^2$; Appendix B). In this case, as the transducer aperture was reduced to 11 mm in diameter, the Doppler power measurement decreased by a factor of 5.0, so that the power measurement must be multiplied by a correction factor of 5.0 before it can be compared with the power of the reference beam to determine the cross-sectional area of the jet at the vena contracta.

In order to determine the ratio between power and area, the backscattered power from the narrow reference beam alternatively can be captured in the filling phase of the mitral valve when the valve is wide open (FIG. 1B); that is because the ratio only requires backscattered power from the flow region of interest independent from velocity. This potentially would ease the application of the PVI approach because placing the reference beam into a small lesion can be difficult. Generally, this indicates that the power measurement with the reference beam in laminar flow can be performed independent of velocity and direction of flow.

The calibration procedure may be simplified by having the two required beams, the narrow reference and the broad measurement beam, generated simultaneously. This is done by taking advantage of a modern digital ultrasound system's capability, the basic principle being as follows: On transmit, the transducer generates a broad and relatively uniform beam that sonifies the entire area of flow as discussed in Appendix D. On receive, the two required beams, the narrow reference and the broad measurement beam, are generated simultaneously by the connection of the transducer elements to two independent digital beam-forming processors. Thus, the Doppler signal information can be acquired and calibrated in a single cardiac phase, thereby eliminating the need to perform a separate calibration operation.

If a measurement of absolute flow is not required, calibration is not necessary. For example, the regurgitant fraction, which is the ratio of regurgitant flow volume to forward flow volume through the valve, can be measured using this non-invasive approach. Measurements are obtained of the regurgitant flow volume and the forward flow volume associated with the valve. Since the measurement of regurgitant fraction consists of the ratio of the two measurements, calibration is not necessary.

System Settings

In all experimental results to now be described, a 2.5 MHZ linear array transducer of 96 elements operating at a Doppler frequency of 1.8 MHZ connected to a Hewlett-Packard 5500 phased array sector scanner was used. The highest-velocity and narrowest-spectrum velocity profile just beyond the regurgitant orifice, from laminar flow at the vena contracta, was recorded with high pulse repetition frequency (high-PRF) Doppler mode with a maximum velocity scale of up to 800 cm/s (for details about high-PRF Doppler see Appendix A). A relatively thin sample volume of axial gate length of 0.35 cm was used and, to prevent signal suppression at low flow rates, a low velocity filter (wall filter) cut-off of 200 Hz (~8 cm/s) was selected. Settings of compress and reject, transmit power, receive gain, depth, and velocity range were kept constant in the entire in vitro series as well as within each patient and animal to allow comparison of returned signals during each series.

Data Recording and Analysis

Doppler spectra were stored digitally, converted off-line to ASCII format and analyzed with MATLAB software (Version 5.1, MathWorks, Natick, Mass.). Power and power times velocity were then integrated over all velocities in the velocity spectrum corresponding to laminar flow in the vena contracta (FIG. 9). In steady flow, PI (power integral) and PVI (power-velocity integral) were computed over each vertical line of the spectral Doppler display (corresponding to a 128-point FFT) and averaging as many as 300 lines in the uncompressed image matrix of power values. For the experiments, each vertical image line represented a time interval of 4.9 ms. In pulsatile flow, the PVI was integrated over time to obtain PVTI (power-velocity time integral) as a measure of regurgitant blood flow volume within one cardiac phase. The difference between PI and PVI is seen in FIG. 9: PI is relatively constant during flow, given the constant in vitro orifice area, whereas PVI, reflecting the flow rate, varies over time and mirrors the velocity as expected for a fixed orifice.

Results

In vitro and in vivo test results for the Doppler power-velocity based technique described above, preceded by a brief explanation of the experimental setup, are presented in the following sections.

In Vitro Setup

Figure 10:
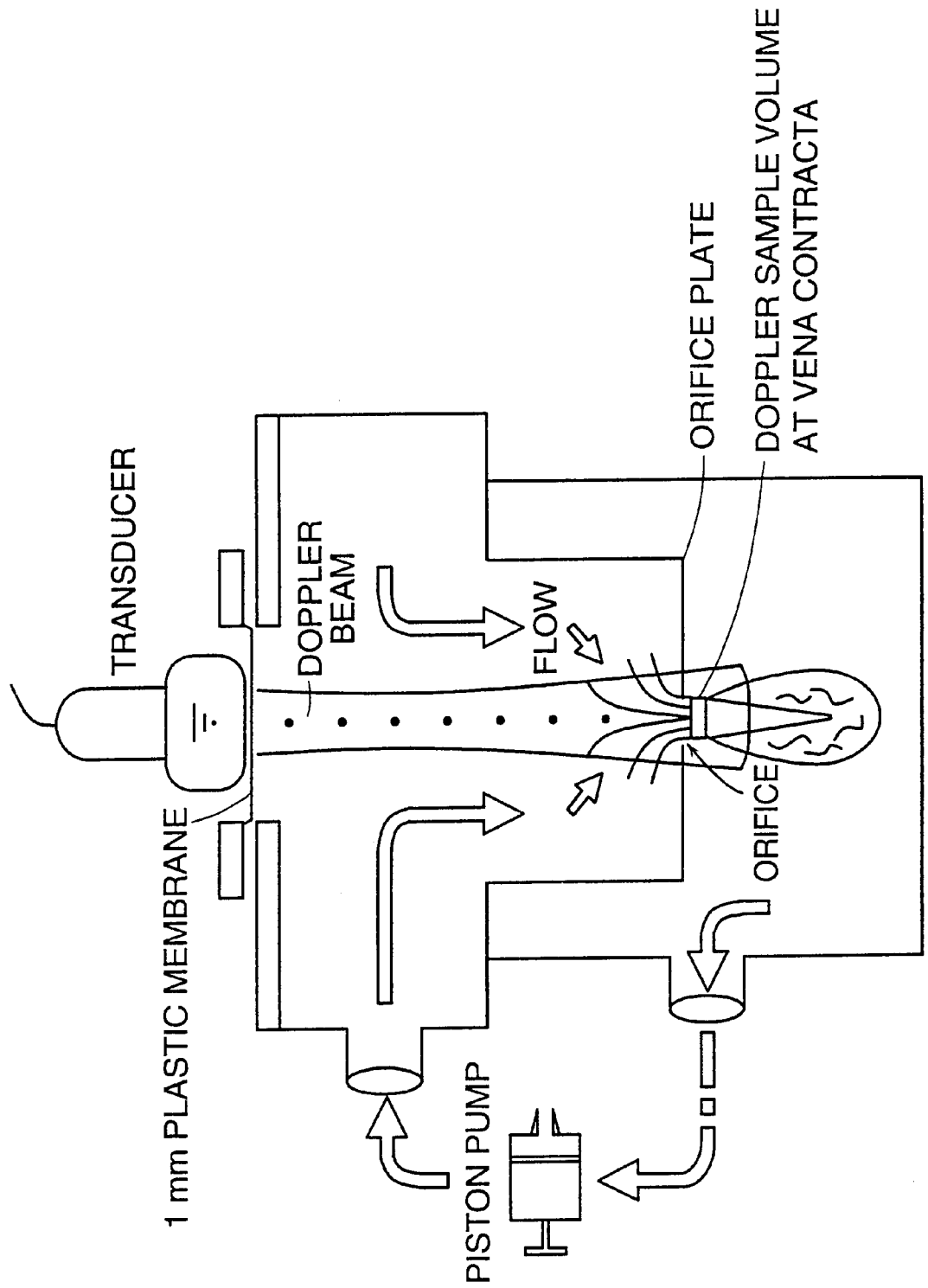
FIG. 10 is a schematic representation of the flow phantom used for in vitro experiments for validation the teaching of this invention.
Figure 11A:
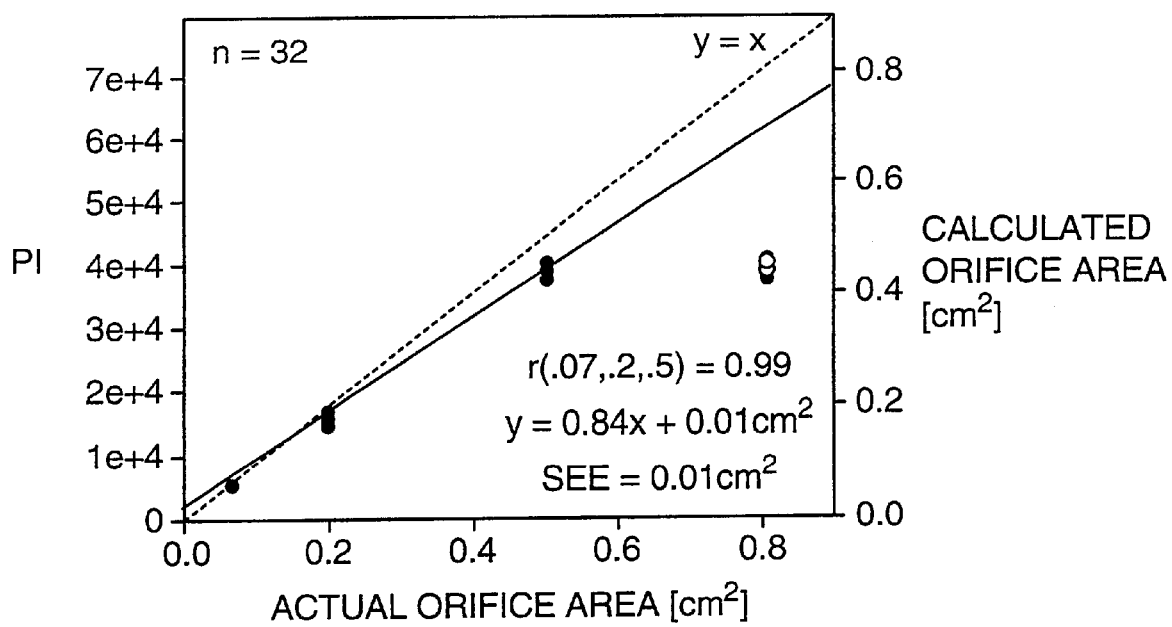
FIGS. 11A and 11B are plots of various results for PI achieved in an in vitro study of this invention.
Figure 11B:
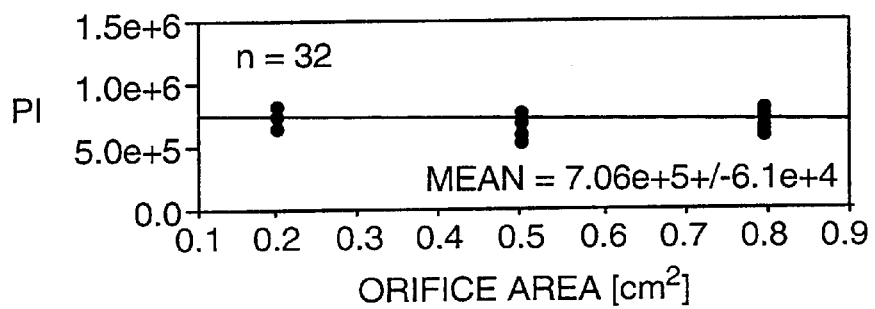

For in vitro validation of the Doppler power-velocity concept for quantification of flow area, flow rate and flow volume for a dynamic orifice, a flow phantom was built to simulate the condition of regurgitant flow at the mitral valve. The flow phantom (FIG. 10) consisted of a variable diameter orifice located 10 cm from the ultrasound transducer acoustic window (typical distance in vivo of a mitral regurgitant orifice from the transducer placed on the chest surface; see FIG. 2A), with flow passing from a large cylindrical chamber (5.7 cm diameter; mimicking the LV) to an unconfined receiving chamber (mimicking the LA). Circular orifice areas of 0.2, 0.5 and 0.8 cm$^2$ were studied at 5 steady flow rates from 20 to 60 ml/s produced by a piston pump (modified Mark IV Powerinjector, Medrad, Inc., Indianola, Pa.) that minimized cavitation, as opposed to impeller-based pumps which were found to produce microairbubbles by cavitation, and with 6 parabolic pulses of regurgitant stroke volumes of 20 to 70 ml (4 different-shaped flow profiles for each stroke volume) produced by syringe injections. Initial studies with outdated blood or blood analogs containing surfactant produced microairbubbles due to cavitation as fluid encountered the pressure drop at the orifice. These microairbubbles severely contaminated the power measurements due to their strong backscattering properties. This was resolved using degassed distilled water with 19% glycerol (resulting specific gravity=1.043 gm/cm$^3$) with a backscattering coefficient equivalent to that of whole human blood, produced by adding 48,600 polystyrene microspheres/ml (25.2 micron diameter; catalog no. DC-25; Duke Scientific Corp., Palo Alto, Calif.).

This flow phantom consisting of two chambers separated by an orifice models the similar condition of valvular stenosis and trans-septal shunting, and hence the results are equally applicable to the application of this procedure to quantification of stenotic valve opening area and shunt area and flow.

In Vitro Results

Figure 12:
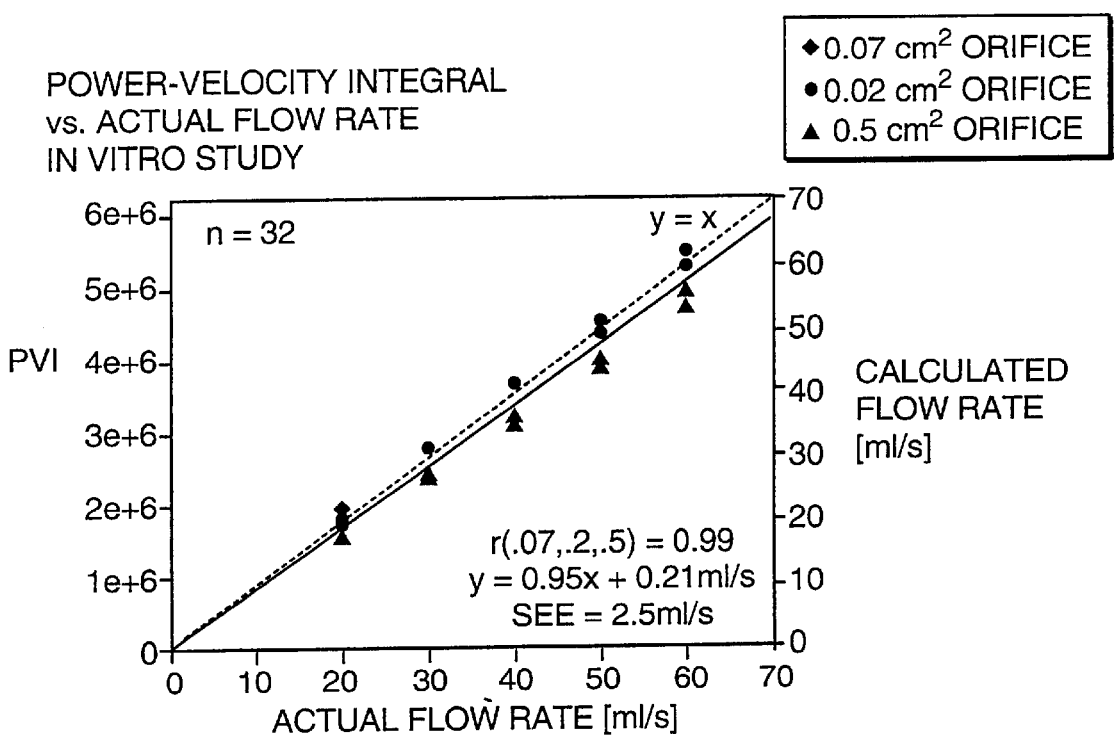
FIG. 12 is a plot of various calculated and calibrated PVI values versus actual flow rates for in vitro experiments involving the teaching of this invention.

For all orifice sizes and flow rates, a clear narrow bright band of intensities at the highest velocities corresponding to the laminar flow at the vena contracta was detected in both steady and pulsatile flow. FIG. 12A shows that, as proposed, there was a linear proportionality between the power integral and the regurgitant orifice area (ROA) up to and including 0.5 cm$^2$ in area (r=0.99); an extreme orifice area of 0.8 cm$^2$ was incompletely measured with the beam size used in the experiments (PI below the regression line for the other orifices). This, however, illustrates the importance of having a measurement beam that is broad enough to fully ensonify the area of the vena contracta.

These power values were measured using the expanded beam created by reducing transducer aperture to a diameter of 7 mm. Calibration was achieved with the narrow reference beam produced by the full aperture. FIG. 12B demonstrates that this narrow beam fit within all the orifices used and therefore returned the same power regardless of orifice area and flow rate over the 32 combinations studied. This narrow beam was then used to create the following calibrations:

$$ROA = c_{cal} \cdot \text{measurement beam PI}$$

$$Q = c_{cal} \cdot \text{measurement beam PVI}$$

$$RSV = c_{cal} \cdot \text{measurement beam PVTI}$$

where $c_{cal}$=(reference beam CSA/reference beam PI) times the correction factor (CF) needed to account for the decrease in power related to aperture reduction (see Eq. 9). The correction factor CF and the reference beam CSA are determined in vitro; only reference and measurement beam PI need to be measured in vivo. In vitro, reference beam CSA was 0.125 cm$^2$ and CF was 63 (Appendix B, 7 mm aperture). With calibration, PI values were converted to regurgitant orifice area (ROA) and correlated and agreed well to actual ROA less than 0.8 cm$^2$ (FIG. 12A, right-hand axis, y=0.84x+0.01 cm$^2$, SEE=0.01 cm$^2$), with slight underestimation of the anatomic orifice areas of 0.2 and 0.5 cm2 since the cross-sectional area of the vena contracta is known to be slightly smaller as determined by a contraction coefficient.

Figure 13:
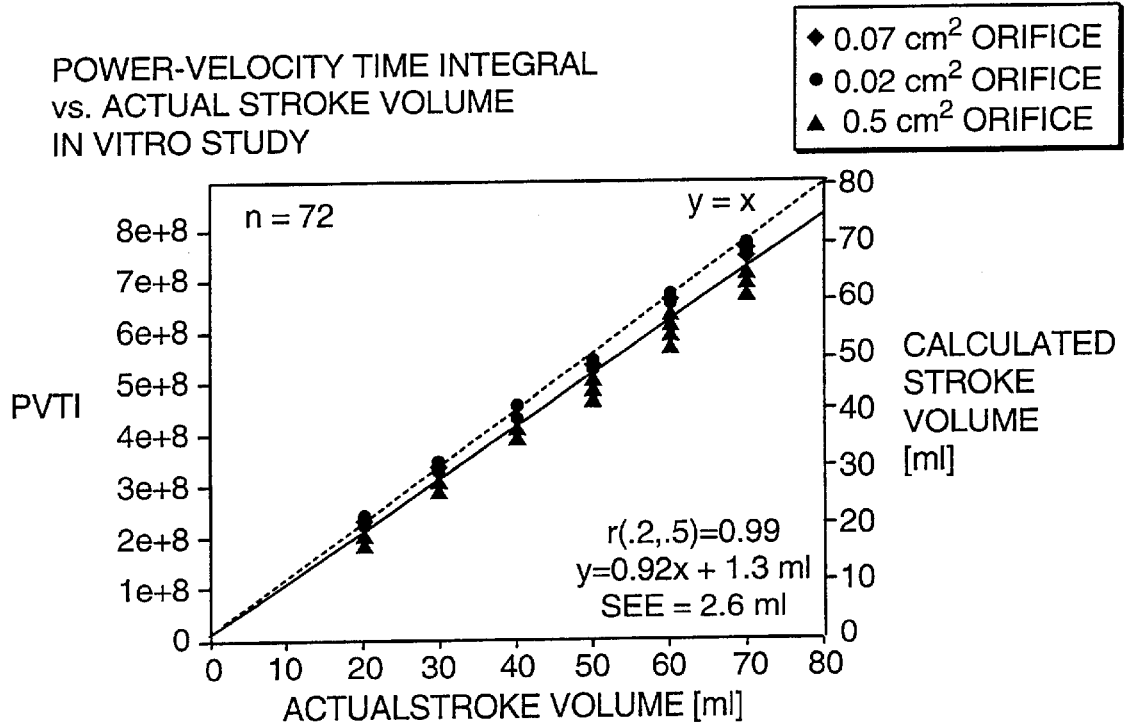
FIG. 13 is a plot of calculated and calibrated PVTI values versus actual regurgitant flow volumes for exemplary in vitro experiments involving the teaching of this invention.
Figure 14:
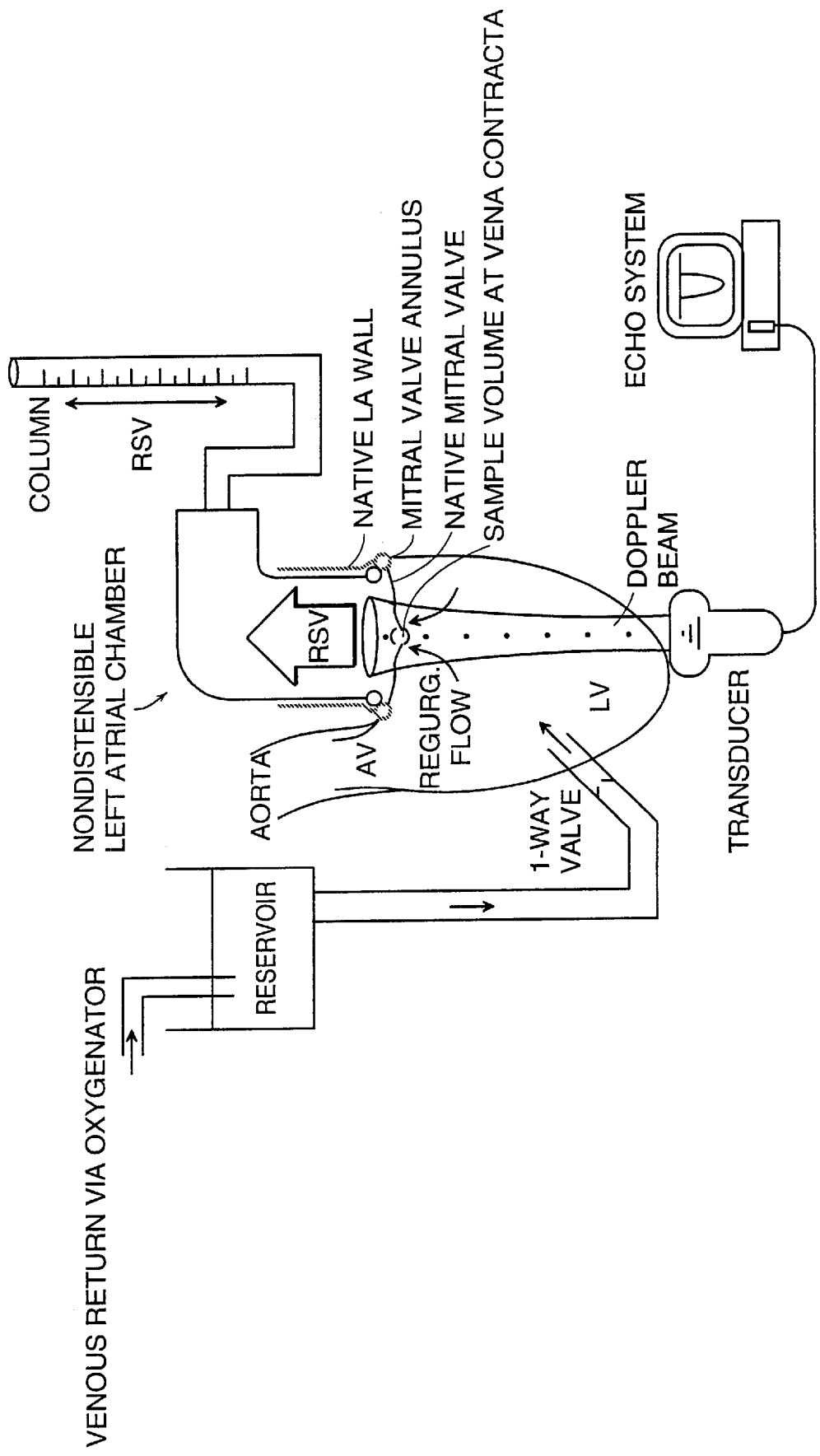
FIG. 14 is a schematic diagram of an in vivo animal model used in performing in vivo experiments involving this invention.

For the 0.07, 0.2 and 0.5 cm$^2$ orifices, flow rates calculated from PVI correlated linearly with actual flow rates (FIG. 13; r=0.99, y=0.95x+0.21 ml/s, SEE=2.5 ml/s). Similar correlation (FIG. 14; r=0.99, y=0.92x+1.3 ml, SEE=2.6 ml) was observed for the 72 studied pulsatile flow volumes calculated from PVTI.

With increasing velocity, a broader velocity spectrum was observed, raising the possibility of turbulent flow. However, as shown in Appendix C, the spectral bandwidth, measured as the central range of velocities in which 95% of scatterers travel (95% of power), was always roughly 20% of the power-weighted mean velocity (PWMV), indicating effectively laminar flow.

In Vivo Experiments

In vivo results are based both on animal experiments and on human patient studies. The animal experiments are presented first. The patient results, including data derived from three-dimensional (3D) ultrasound and magnetic resonance imaging (MRI) techniques for independent reference follow.

Animal Study Setup

Figure 15:
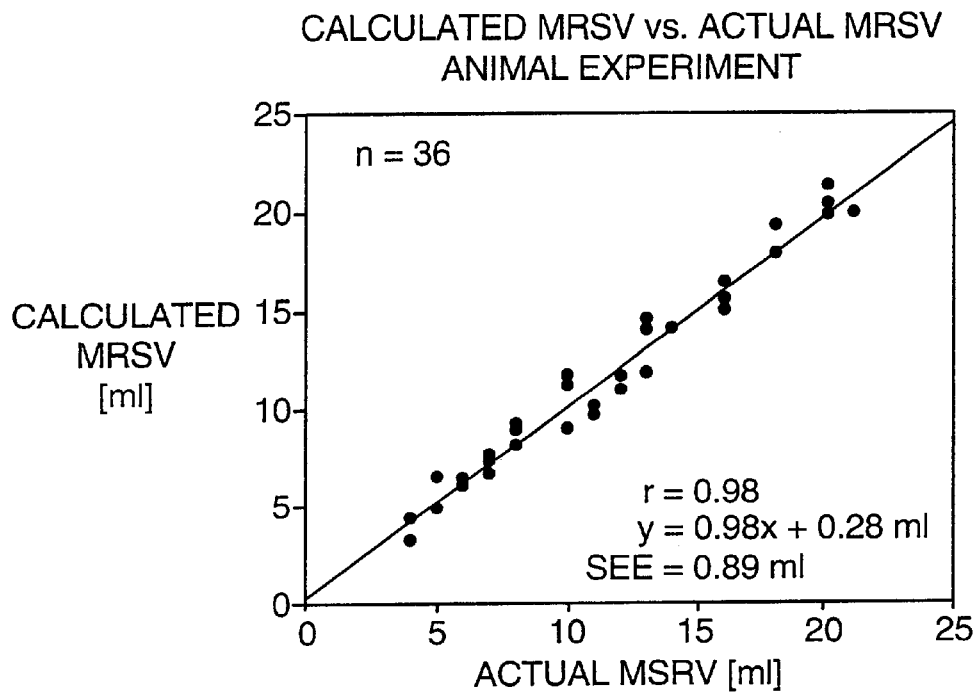
FIG. 15 is a plot of calculated and calibrated mitral regurgitant stroke volume (MRSV) versus actual values of MRSV for in vivo animal experiments.

In order to retain the native leaflets of the mitral valve, most comparable to the physiologic situation, and to measure MR volume directly, we developed the new canine model (FIG. 15). A nondistensible left atrial chamber was sutured to the native mitral annulus via a Dacron sewing ring, and the atrial walls sutured tightly around it to prevent leaking. This chamber was attached via nondistensible tubing to a vertical 1.0 cm diameter column. In the presence of a rigid left atrium, the entire MR stroke volume (MRSV) produced a vertical fluid excursion in the attached column with each systole (1.3 cm=1 ml), this excursion was videotaped and measured. Using this system, a total of 36 different hemodynamic stages were analyzed in 3 dogs, in each of which a regurgitant orifice of different size (0.12 to 0.21 cm$^2$) was cut into the anterior mitral valve leaflet and afterload changed by clamping the aorta to vary the amount of regurgitant flow.

All procedures were approved by the institutional Animal Care Committee based on NIH (National Institute of Health) principles.

Animal Study Results

Figure 16A:
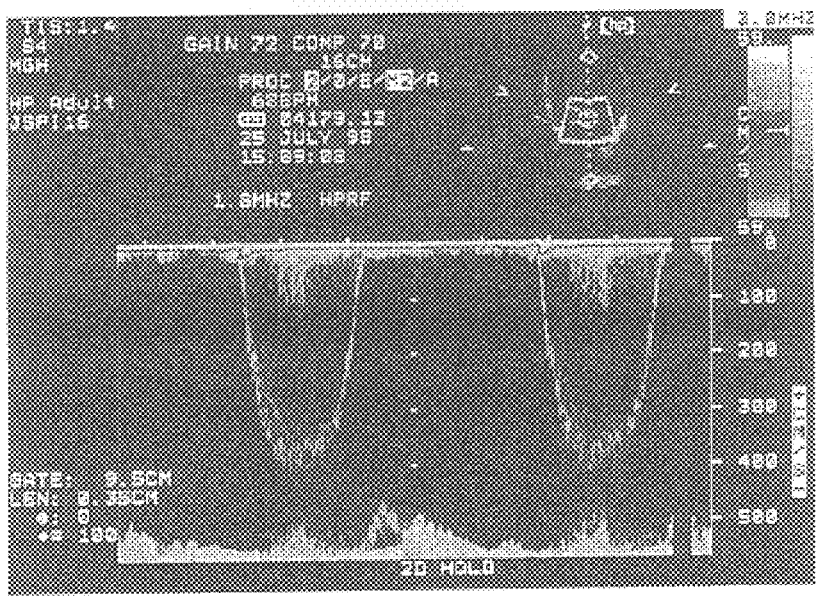
FIGS. 16A–16C are illustrative Doppler spectra for a patient with functional mitral regurgitation.
Figure 16B:
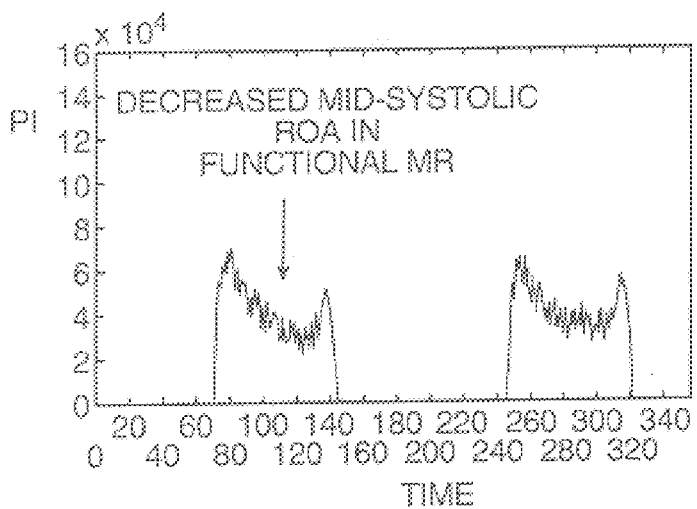
Figure 16C:
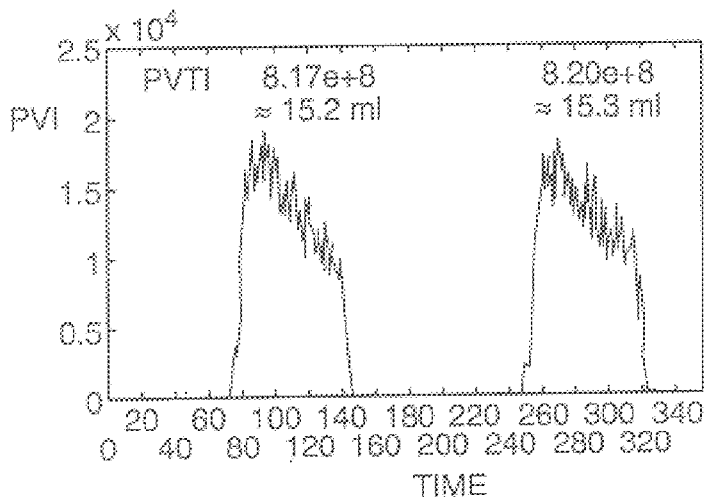

During each hemodynamic stage, regurgitant stroke volume as measured based on the video camera recordings was stable over the time of recording (10–20 cycle). FIG. 16 shows results for MRSV calculated from the power measurements versus directly measured values of MRSV (left atrial column excursions) for 36 hemodynamic stages in all three animals. Actual values of mitral regurgitation stroke volume ranged from 4 to 21 ml.

Calculated and actual values correlated excellent (y=0.98x+0.28ml, r=0.98, SEE=0.89 ml).

Patient Study Setup

To demonstrate that the Doppler power principle can in fact be applied in patients, the amount of mitral regurgitant flow volume (MRSV) that occurs in each systolic phase of the heart cycle was determined in eleven patients (age 65±13 years; 8 male, 3 female) with at least mild to moderate mitral regurgitation of different etiologies, using the same methods applied in vitro. In all patients, values for MRSV by Doppler power were compared with those calculated from left ventricular ejection volume by three-dimensional echocardiography minus forward aortic stroke volume derived from left ventricular outflow tract CSA times the time integral of the power-weighted mean velocity measured in the LV outflow tract, which takes into account the velocity spectrum within the beam. PVI measurements were also compared with estimates of mitral regurgitant stroke volume obtained using MRI in three patients. To date the MRI approach represents the most trusted procedure for quantification of regurgitant flow. However, it is extremely time consuming, requiring patient confinement within the bore of the magnet of 1 hour, and is prohibitively expensive and not practical for this application.

Patient Study Results

Figure 17:
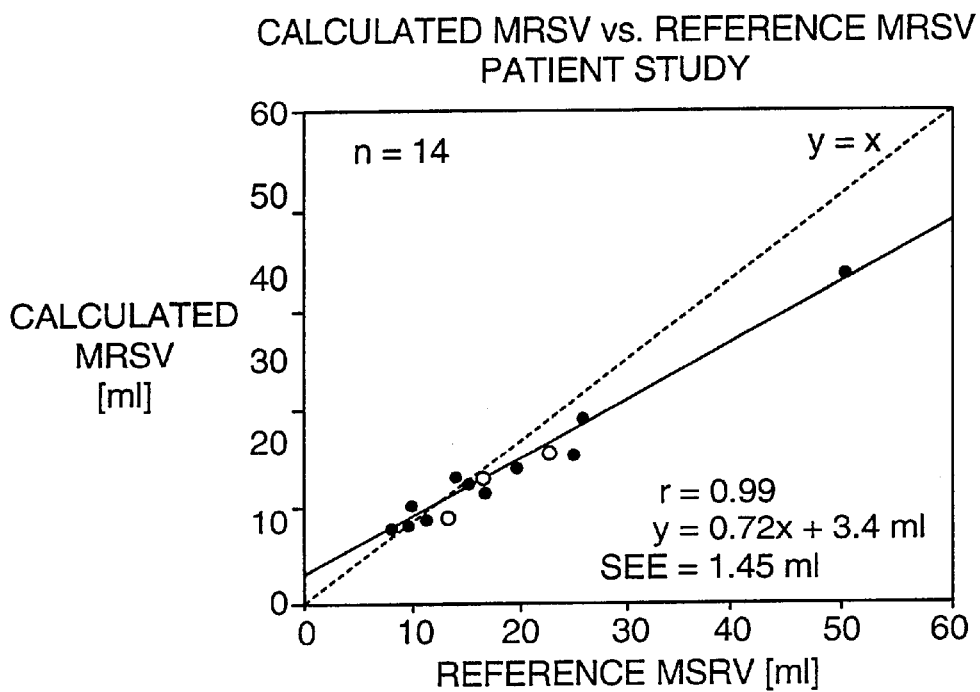
FIG. 17 is a plot of calculated and calibrated mitral regurgitant stroke volume (MRSV) versus independent reference values of MRSV in patient studies.

In all patients, a satisfactory high-PRF Doppler signal with a narrow velocity spectrum from laminar flow at the vena contracta was obtained; including those with eccentrically directed jets. FIG. 17 shows an example of such a velocity spectrum in a patient with functional mitral regurgitation. Of note is that the power integral has early and late systolic peaks and mid-systolic decrease, which is the recognized pattern for regurgitant orifice area in such patients since the two valve leaflets are pushed together in mid-systole by the peak LV pressure, which decreases the orifice area.

Figure 18A:
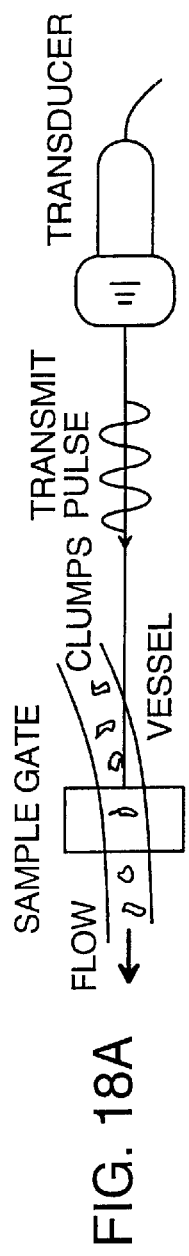
FIG. 18A is a schematic structure presentation, and FIG. 18B are plots useful in conjunction with Appendix A for describing the principles of pulse Doppler for blood velocity measurement.
Figure 18B:
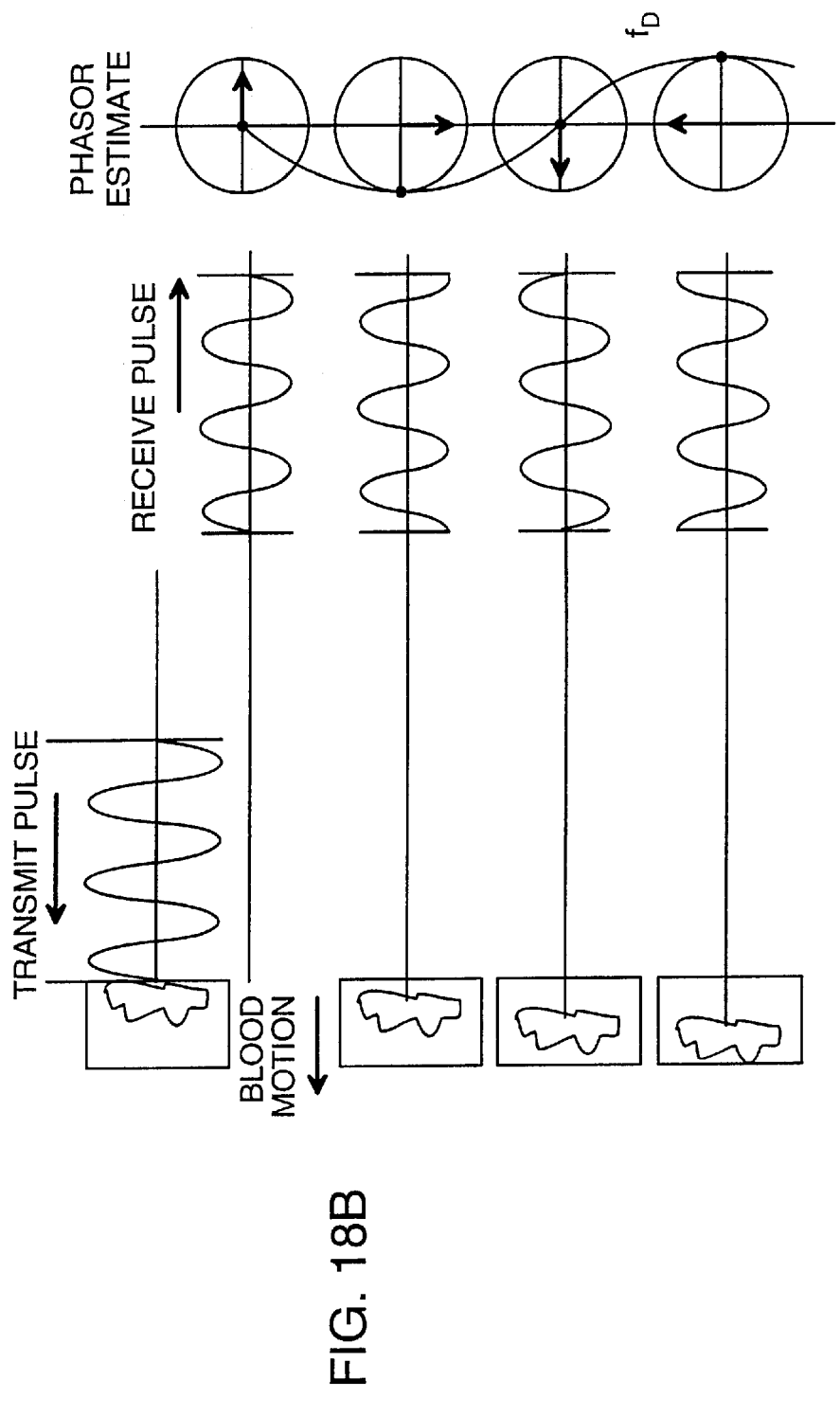

Values of mitral regurgitant stroke volume in the eleven patients as measured by the reference techniques ranged from 8.0 to 50.1 ml representing mild to severe regurgitation. Correlation between the PVTI estimates of MRSV and reference values are shown in FIG. 18 (r=0.99, y=0.72x+3.4 ml, SEE=1.45 ml). The correlation is good for flow volumes up to 20 ml. However, there is underestimation of regurgitant volumes above 20 ml that is attributed to the limited measurement beam size used in these experiments; that is, the larger regurgitant flow volumes correspond to large regurgitant orifices which exceeded the cross-sectional area of the measurement beam. It is anticipated that with a broader measurement beam this underestimation of the higher regurgitant stroke volumes can be eliminated.

Conclusions

Ultrasound over the past twenty years has proven to be extremely valuable as a noninvasive medical diagnostic tool not only for cardio-vascular diseases but also for prenatal and gynecologic examinations, and for diseases of the liver and kidneys among others. Some new uses include tissue characterization, breast cancer identification, and eye examinations. However, though the target of many researchers worldwide, the direct and noninvasive quantification of regurgitant pathologic volume flow in the human heart is still not possible. Existing ultrasound approaches, either based on simplification of the regurgitant pathologic flow model or on complex multi-step procedures, do not measure the flow directly at the lesion of the valve and have failed to provide satisfactory results. For example, direct measurement of the regurgitant flow, is dependent upon the knowledge of the area of flow, which is difficult to measure due to its complex and dynamically changing geometry; until the development of this invention no ultrasound technique has been available to provide such a measurement in a reliable and useful manner.

The innovative approach of this invention is based on the integral of backscattered acoustic power, which, in principle, provides a measure of flow cross-sectional area. Although the basic physics of flow and ultrasound indicate the integral of Doppler power times velocity can measure flow rate and flow volume, investigators have felt this principle could not be applied to regurgitant pathologic jets comprised of high-velocity flow in the human heart because backscattered power is variably increased by turbulence and entrainment of fluid. For that reason previous studies using Doppler power evaluated only flows that were restricted to a conduit (tube, large vessel, or ventricular outflow tract) and therefore considered laminar. This invention demonstrates that this limitation can be overcome by integrating power times velocity in the narrow velocity spectrum obtained from flow passing through a thin sample volume placed in the vena contracts, that is, at the origin of the regurgitant jet, where flow is mostly laminar since turbulence has not yet developed.

The approach of this invention has several advantages. First, regurgitant flow rate and volume can be measured using only the backscattered power and velocity information as obtained by ultrasound Doppler. Because, integrating backscattered power times velocity over the Doppler spectrum automatically contains a measure of the flow cross-sectional area due to the proportionality of backscattered power to flow area, this approach overcomes the limitations of most techniques that require a separate area measurement. Second, the thin Doppler sample volume can be placed directly at the lesion where regurgitant flow occurs, making possible the most direct and therefore accurate measurement of regurgitant flow area and flow volume. Third, with this approach there are no simplifying assumptions about the velocity distribution across the flow area, because the Doppler beam effectively integrates all incremental areas of different flow rates. There are also no concerns about the spectrum of velocities because the approach integrates backscattered power times velocity over the entire velocity spectrum, as long as the spectrum is reasonably narrow indicating mostly laminar flow. Finally, the power-velocity measurement, is independent from variations in the angle $\theta$ between the direction of flow and the main axis of the Doppler beam. It has been shown that this principle is correct at least for angles from 0 to 45°.

It is important to realize that the size and shape of a regurgitant orifice in vivo is varying throughout the period of regurgitation, thereby limiting the ability of existing techniques which rely upon a single estimate of the orifice area, since no satisfactory procedures were available to record these dynamic changes. The beauty of the PVI approach is that, because the Doppler beam effectively integrates all incremental areas of different flow rates independent of their local distribution across the beam area, there are no longer concerns about the complex shape and size of the dynamic flow cross-sectional area or the regurgitant orifice. This is also important because different shapes and sizes of regurgitant orifices caused different complex flow fields around the valve lesion thereby limiting the accuracy of other techniques based on rather simplistic geometric flow field assumptions.

This concept was applied in an ideal in vitro environment, in a more realistic experimental in vivo setting with a direct goldstandard, as well as in patients, with very good results, demonstrating a linear proportionality between flow cross-sectional area and the Doppler power integral (PI), between regurgitant flow rate and the integral of Doppler power times velocity (PVI), and between regurgitant stroke volume and the time integral of the integral of Doppler power times velocity (PVTI), all measured directly at the vena contracta. These results, and the narrow velocity spectra observed even for relatively small orifices and eccentric jets in patients, suggest that no significant turbulence develops at the vena contracta that would interfere with this proportionality. Besides demonstrating the proof of the PVI concept, the practicability and accuracy of this new approach was successfully demonstrated in patients with various mitral valve diseases leading to mitral regurgitation.

Future systems may be developed which simplify the procedure for routine clinical application. The described system has an ultrasound transducer capable of creating a broad and uniform measurement beam and a narrow reference beam for calibration purposes. Thereafter a manual, partially automated or fully automated analysis of the Doppler signal is performed by the system, identifying the narrow Doppler spectrum associated with laminar flow in the vena contracta and calculating PI, PVI, and PVTI. Finally, the results of the measurement beam are calibrated taking into account transmit power, receive gain, and other relevant system settings, thereby producing and displaying measurements of diagnostic importance such as peak cross-sectional area of flow, mean cross-sectional area of flow, peak flow rate, mean flow rate, stroke volume and regurgitant fraction.

Beyond the presented application in mitral valve regurgitation, this new concept can be applied to other diseases associated with flow through dynamic orifices; for example regurgitant flow of each of the four heart valves, as well as valvular stenosis, septal defects with shunt flow, and peripheral vascular disease with vessel obstruction, where valvular stenosis refers to restricted forward flow due to a condition that prevents the valve from opening completely and a septal defect refers to a pathologic orifice in the septum that separates the right and the left side of the heart. In particular, accurate noninvasive measurement of stenotic (restricted) valve opening areas based on the calibrated power integral would critically improve diagnosis and treatment of stenotic valve disease. Ultimately, this PVI approach could be used to obtain regurgitant fraction as the ratio of regurgitant flow volume to normal forward flow volume; this would require a beam encompassing the cross-sectional area of forward flow when the valve is open. The beauty of this approach would be that both regurgitant and forward volume could be determined from the same sample volume. By adding regurgitant and forward flow volume at the mitral valve, cardiac output, one of the most important clinical parameters, is obtained, where cardiac output refers to the volume of blood pumped by the heart in a cardiac cycle.

Thus, the PVI concept can overcome the limitations of existing techniques that are invasive, costly, and inaccurate and has the potential to replace them.

APPENDIX A

Principle of pulsed Doppler for Blood Velocity Measurement

The spectral Doppler modality as used in diagnostic ultrasound is not exactly based on the concept that the frequency of a signal field radiating or reflected from a moving source differs from that radiated or reflected from a stationary source. Rather, in the ultrasound spectral Doppler modality of blood velocity estimation, the estimate of blood velocities is derived from a series of estimates of phase shifts related to displacement of the scattering blood due to its motion. A simple description of the procedure follows.

Consider the case of blood flowing within a vessel. The ultrasound beam is steered and focused to a small sample volume of blood within the vessel (FIG. 18). This is done by manually positioning a 'gate' in the two-dimensional image of the vessel where the Doppler measurement is to be made. The lateral dimension of the sample volume identified by this gate is a function of the width of the acoustic beam, which in turn has a dependence upon the aperture of the transducer, that is, a larger aperture produces a narrower beam width at the focal point. Based on the distance of the sample volume from the transducer, the system determines a round-trip travel time of the ultrasound signal. The system begins to process the backscattered signal using the round-trip travel time relative to the time of transmit and processes it for a period of time determined from the thickness of the sample volume as defined by the operator controlled gate thickness.

For the Doppler mode required for this method of flow quantification, referred to as pulse-wave Doppler (PW), the signal is a sinusoidal pulse that is transmitted and backscattered continuously as it propagates forward (FIG. 18). The time duration of the transmitted pulse is commonly six to twelve periods of the sine wave in the PW mode of spectral Doppler. The reason why a pulsed signal is required is to define a distinct sample volume of interest. That is, in the PW mode, the pressure field at the receiving transducer at any time is attributable only to backscattering blood at a certain depth corresponding to the distance from the transducer determined by the round-trip travel time, capturing only the signal from flow through the lesion. If a continuous signal is transmitted, the spectrum incorporates all blood flow along the entire path of the beam including extraneous flow not associated with the lesion.

After electronic beam-forming of the received signal, the amplitude and phase of the acoustic signal pulse backscattered from the sample volume are determined. The phase is determined relative to the time of transmit in order to utilize the phase information between successive pulses to estimate blood velocity (FIG. 18). That is, the difference in phase relative to the previous pulse results from the motion of the blood within the sample volume. Therefore, after a period of time sufficient for the transmitted pulse to propagate to the sample volume and return to the receiver, a subsequent similar pulse is transmitted and an estimate of the phase of the received backscattered signal is determined in order to construct a series of such measurements needed for reliable estimates of velocity.

Next, a brief explanation of the backscattering concept is provided. The red blood cells are clumped together as they pass through the sample volume and each clump acts much like a distinct target reflecting the transmitted pulse. The reflected pulse has nearly the same frequency on transmit and receive, because the blood velocities are too slow in relation to the high ultrasound frequency to compress or elongate the wavelength (Doppler effect). However, over a series of pulses each clump imparts a distinct phase on the signal, which remains similar from pulse to pulse throughout the duration of the clump in the sample volume. Hence, the phase difference detected is associated with the propagation of the individual clumps (FIG. 18). The phase difference, $\Delta\phi$, is given by $$\Delta\phi = \frac{2\Delta R}{\lambda}$$

where $\lambda$ denotes the spatial wavelength of the sinusoidal pulse and $\Delta R$ denotes the change in the range to the reflecting blood due to motion. The factor of two accounts for the round-trip propagation path difference. For the sinusoidal pulse, the wavelength is c/f where c denotes the speed of propagation of sound within the medium and f denotes the frequency of the sinusoidal pulse. The change in range between pulses is given by $$\Delta R = v \cos\theta \times \Delta t$$

where v denotes the speed of the blood, $\theta$ denotes the angle between the direction of blood flow and the direction of sound propagation, and $\Delta t$ denotes the time between pulses. Hence, the phase difference can be expressed as $$\Delta\phi = \frac{2vf\cos\theta \times \Delta t}{c}$$

or equivalently, $$\frac{\Delta\phi}{\Delta t} = \frac{2vf\cos\theta}{c}$$

where $f_D$ denotes the Doppler shifted frequency. This is the expression used to relate the Doppler frequency to the velocity of blood in the sample volume. The velocity spectrum of moving scatterers in the sample volume is then derived from the received composite signal frequency spectrum, commonly derived using an FFT procedure.

The reason for waiting for the transmitted pulse to return to the receiving transducer before transmitting a subsequent pulse is to avoid ambiguity. That is, if a pulse is transmitted before the previous pulse completes the round-trip to the sample volume, the received signal within the processing time window corresponding to the sample volume would contain the desired backscattered signal as well as the backscattered signal corresponding to the more recent pulse. Clearly, the backscattered signal associated with the more recent pulse is backscattered from a smaller depth than the sample volume.

There is an additional important source of ambiguity associated with PW Doppler, referred to as aliasing. Aliasing occurs when the velocity of the blood is such that the phase difference between successive pulses is greater than 180 degrees of the sinusoidal period. When this occurs there is an ambiguity of blood flow direction and velocities. For example, a phase difference of 200 degrees could equally well be interpreted as motion in the opposite direction producing a phase difference of 160 degrees. This condition of aliasing is identical to the aliasing that occurs when a waveform is under-sampled; that is, the Nyquist criterion is not met. In PW Doppler, this occurs when the pulses are transmitted at too low a rate (PRF, pulse repetition frequency) such that the distance traversed by the blood between pulses produces a phase difference of greater than 180 degrees thereby producing an ambiguity. The low pulse rate is usually imposed by the time required for the round-trip propagation to the sample volume of interest and back.

However, it is possible to ignore the round-trip propagation time constraint and to select a transmit pulse repetition frequency sufficiently high to eliminate velocity aliasing. This spectral Doppler mode is called high-PRF referring to the high rate of transmission of the individual pulses. Although the velocity ambiguity (aliasing) is eliminated, an ambiguity in the depth of the source of the backscattered signal is introduced. This depth ambiguity can be explained as follows.

To avoid velocity aliasing, pulses are transmitted with PRF=1/Δt where the PRF is sufficient to avoid aliasing, but the time between successive pulses, Δt is less that the round-trip travel time required. Hence, when the system is receiving the backscattered signal corresponding to the round-trip travel time to the volume of interest from pulse $P_n$, there is also backscattered signal present from the successive pulse, $P_{n+1}$. Clearly, the signal associated with pulse $P_{n+1}$ is backscattered from a shallower depth than pulse $P_n$.

Two factors contribute to the reduction in the spatial aliasing associated with high-PRF. First, the transmit and receive beam-forming are focused to the depth of the volume of interest, providing a degree of spatial discrimination with respect to the regions that are not in focus. And secondly, if the backscatter from the undesired region is not from blood flow, it will not contaminate the spectrum from which the velocity information is derived. The spatial aliasing associated with high-PRF is not limited to a two pulse scenario. Often times the velocities to be measured are sufficiently high to necessitate the transmission of three or more pulses within the round-trip travel time interval.

There is also a continuous wave (CW) mode that transmits a sinusoid continuously which is not discussed here. In the CW mode, the pressure field at the receiving transducer at any time is attributable to backscattering occurring throughout the path of signal propagation, and hence is not suitable for quantification of flow within the valve lesion.

APPENDIX B

Correction factor for Aperture Size Reduction

Figure 19:
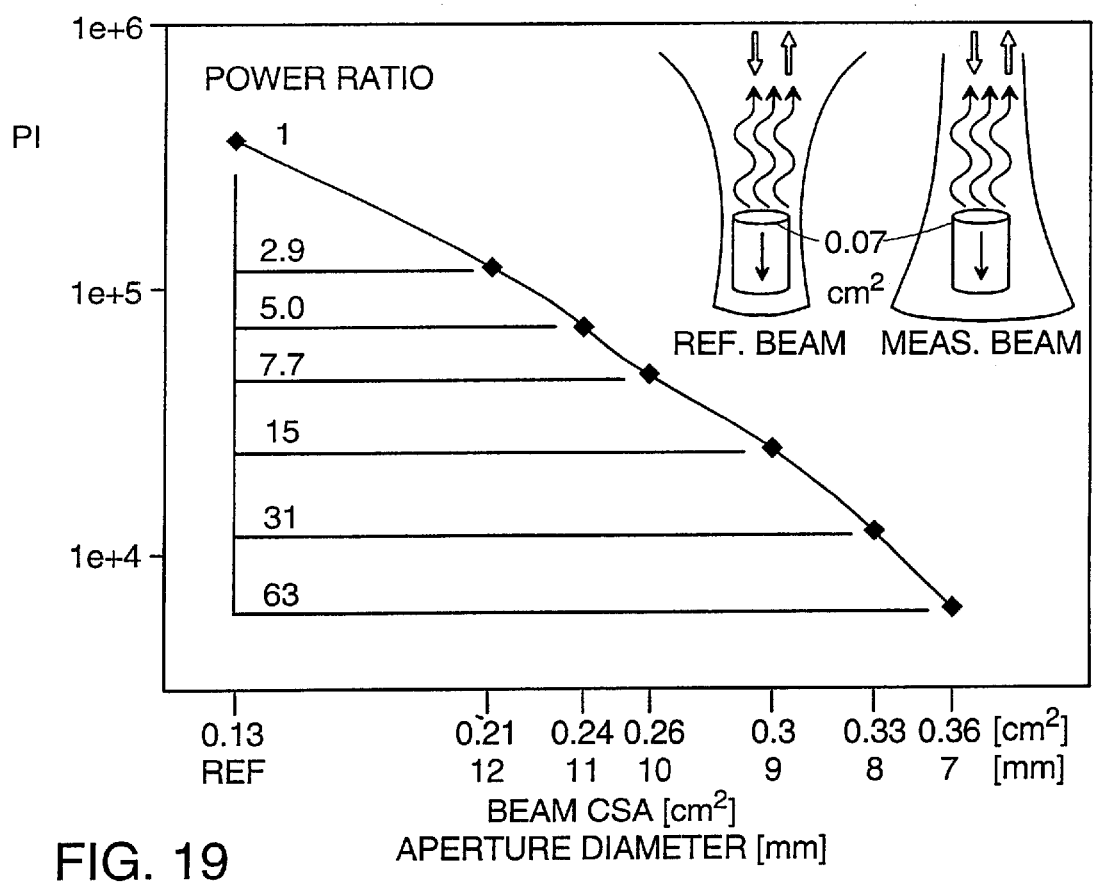
FIG. 19 is a plot useful in conjunction with Appendix B for illustrating beam properties, and in particular the use of a smaller aperture to produce a larger beam CSA.

The PVI approach requires a broad measurement beam which was realized by decreasing the transducer aperture. This reduced the transmit power level and the received signal sensitivity relative to the full aperture reference beam. The ratio of reference beam power to measurement beam power resulting from the aperture size differences must be known and corrected for in order to obtain absolute measurements of flow. The power ratio was obtained by ensonifying flow through a small orifice of cross-sectional area (0.07 $cm^2$) being less than the width of both beams, the narrow reference and the broad measurement beam (FIG. 19). The power ratio, although depth dependent, was determined for a depth of 10 cm, which is the typical depth of the mitral valve of an adult.

APPENDIX C

Narrow Band Power Spectrum at the Vena Contracta

Figure 20:
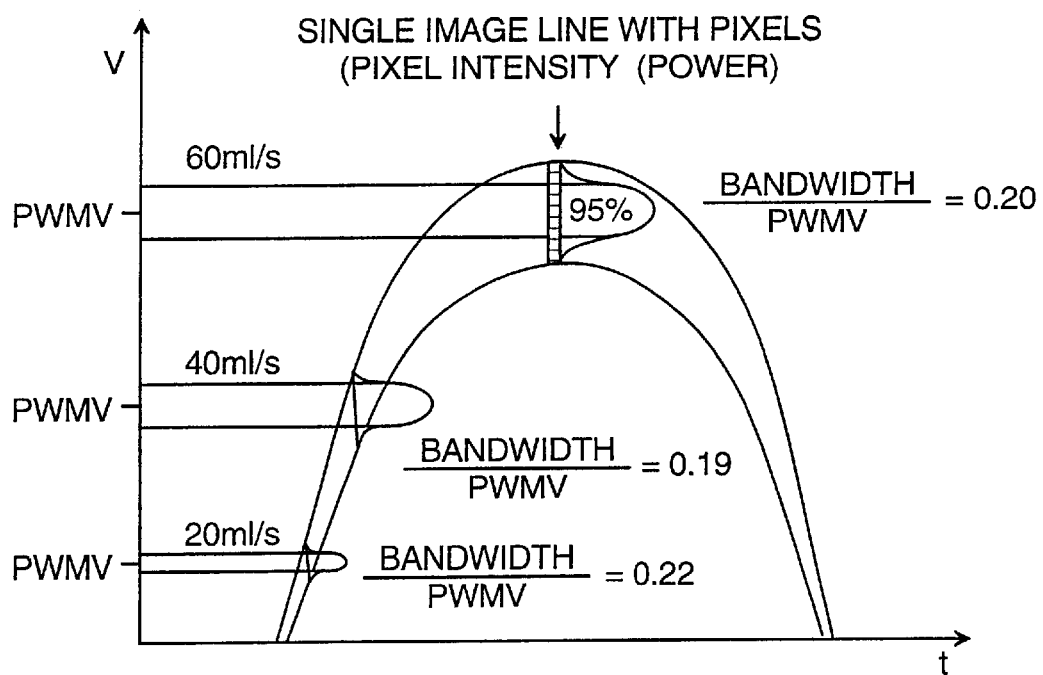
FIG. 20 is a plot useful in conjunction with Appendix C for understanding broadening of the power-velocity spectrum of laminar flow.

The vena contracta denotes the region adjacent to the orifice where flow is mostly laminar and turbulence and entrainment have not yet occurred. The limited range of velocities associated with this condition produce a narrow band power spectrum (FIG. 20). Although the spectrum appears broader at the higher velocities, the ratio between the velocity spectral bandwidth (as the central velocity range in which 95% of scatterers travel) and the power-weighted mean velocity (PWMV) remains constant as indicated in the figure. Using actual spectral PW Doppler data, the bandwidth was found to be approximately 20% of the power-weighted mean velocity. This behavior is characteristic of laminar flow as opposed to turbulent flow.

APPENDIX D

Beam Broadening

The methods described for noninvasive quantitative measurement of flow volume (blood volume passing through an orifice) and cross-sectional area require, as one step, the measurement of flow rate based on the power-velocity integral concept. This concept requires that the two-way measurement beam response (sensitivity) corresponding to the Doppler signal frequency band be uniform over the cross-sectional area of flow. Depending upon the application, the cross-sectional area of flow can be as much as two to three centimeters in diameter.

Since the two-way response is the product of the transmit and receive response patterns, in theory the transmit and receive beam patterns each can be non-uniform as long as their product is uniform. However, it is best to ensonify the cross-sectional area as uniformly as possible so as to maintain a signal power to noise power ratio sufficient for reliable signal detection and flow estimation over the cross-sectional area of flow. Therefore, we focus primarily on synthesis procedures that produce uniform one-way beam sensitivity.

There are various methods for controlling the shape of the beam pattern; use of a mechanical lens, defocusing, and apodization to name a few. Apodization, which is well suited to phased array transducers, is the procedure of applying a gain factor to each discrete element of the array. Through the appropriate setting of each of these gain factors, the beam shape can be controlled within limits. In general, the gain factor is complex, that is, it consists of both amplitude and phase. If the Doppler signal occupies a sufficiently wide band of frequencies it may be necessary to synthesize two-dimensional apodization functions, being both a function of array element location and frequency. For example, in the simplest case, the pointing direction and focus of a narrow-band beam can be controlled by applying a complex gain that consists solely of the appropriate amplitude and phase shift to each array element.

One apodization function in particular, known as the Chebycheff function, produces a maximally uniform main-beam response. Hence, the synthesis and application of such an apodization function would produce the desired beam condition. Note however, that the array must be apodized in both the elevation and lateral dimension and hence must be a two-dimensional phased array. Such arrays are expensive and only now beginning to show signs of promise for future applications, in particular, three-dimension ultrasound imaging. In addition, the synthesis should be conducted with respect to the two-way beam response.

Since the cost of a two-dimensional array is probably prohibitive presently, an alternative is needed. Such exists. One approach is the use of a 1.5-dimensional array. Such an array achieves limited control in the elevation dimension by having five discrete elements in the elevation dimension and sixty-four in lateral for example. To minimize cabling requirement, furthermore, symmetric rows are connected together pairwise, that is, rows one and five and rows two and four, thereby disabling electronic steering in the elevation dimension. In this configuration, Chebycheff apodization can be applied in the lateral dimension and limited apodization can be applied in the elevation dimension for both transmit and receive to control the overall beam response.

The final approach presented consists of using a mechanical fixed lens to the phased array. Since control exists in the lateral dimension, Chebycheff or some other desirable apodization can be applied to control the lateral beam response. The mechanical lens is applied to control the elevation response. However, since the mechanical lens is fixed, a compromised is require so as to achieve elevation beam characteristics that are suitable for both the measurement beam and the much narrower reference beam.

While the invention has been shown and described above with reference to illustrative embodiments, the foregoing and other changes in form and detail may be made therein by one skilled in the art while still remaining within the spirit and scope of the invention which is defined only by the appended claims.

What is claimed is:

1. A method for obtaining an area for a dynamic orifice through which blood is flowing in at least one direction comprising:
   a) ensonifying a sample volume of blood flow exiting the orifice, which volume is in a region of said flow which is substantially laminar, with an ultrasonic pulsed Doppler signal;
   b) receiving backscattered signal from blood within said sample volume;
   c) forming a power-velocity spectrum from received backscattered signal; and
   d) forming an instantaneous power integral of laminar flow for the power-velocity spectrum, said power integral being proportional to instantaneous cross-sectional area of the orifice.

2. A method as claimed in claim 1 including (e) determining the portions of laminar flow in said power velocity spectrum.

3. A method as claimed in claim 2, wherein step (e) includes (e') identifying a narrow velocity spectrum of laminar flow to be used in forming the power integral, said step (e') including:
   (i) smoothing the power-velocity spectrum;
   (ii) determining the velocity of peak power in a smoothed power-velocity spectrum;
   (iii) determining a lower velocity of laminar flow, said lower velocity being a selected velocity less than the velocity for peak power where the power is a specified percentage of the peak power; and
   (iv) determining an upper velocity of laminar flow, said upper velocity being a selected velocity greater than the velocity of peak power where the power is a specified percentage of the peak power.

4. A method as claimed in claim 1, wherein said sample volume is at the vena contracta of flow exiting the orifice.

5. A method as claimed in claim 4, including the step (f) of steering and focusing the ultrasonic signal to said vena contracta.

6. A method as claimed in claim 5, wherein step (f) includes utilizing an image mode display of backscattered signal to steer and focus the signal to the vena contracts, and utilizing at least one of a Doppler mode power/time display and audio signal to fine tune steering/focusing of the ultrasonic signal to the vena contracts.

7. A method as claimed in claim 1, wherein said ultrasonic signal to be used for said power integral measurement ($PI_{meas}$) is wide enough to fully ensonify the cross-sectional area of the laminar flow.

8. A method as claimed in claim 1, including repeating steps a), b), c) and d) to obtain a profile of flow area over time.

9. A method as claimed in claim 1, wherein said flow is regurgitant flow though a faulty heart valve, the orifice area being that of lesions in the heart valve permitting the regurgitant flow.

10. A method as claimed in claim 1, wherein said flow is stenotic flow through a restricted heart valve, the orifice area measurement being the restricted valve opening area permitting the flow in normal direction through the valve.

11. A method as claimed in claim 1, wherein said flow is shunt flow through a shunt lesion, the orifice area measurement being of shunt lesions permitting the shunt flow.

12. A method as claimed in claim 1, wherein said flow is stenotic flow through a restricted peripheral vessel, the orifice area measurement being the restricted area of flow.

13. A method as claimed in claim 1, including the step of (g) of calibrating to permit absolute area of laminar flow to be obtained.

14. A method as claimed in claim 13, wherein step (g) includes applying a narrow ultrasound reference beam within said region, said reference beam having a known CSA ($CSA_{ref}$), and computing Flow CSA from Flow CSA= $CSA_{ref} \cdot PI_{meas}/PI_{ref}$.

15. A method as claimed in claim 14, wherein said flow is regurgitant flow through a faulty heart valve, and wherein step (g) includes detecting Doppler ultrasound power from said reference beam when the valve is open for forward flow.

16. A method for obtaining flow rate of blood passing through a dynamic orifice in at least one direction comprising:
   a) ensonifying a sample volume of blood flow exiting the orifice, which volume is in a region of said flow which is substantially laminar, with an ultrasonic pulsed Doppler signal;
   b) receiving backscattered signal from blood within said sample volume;
   c) forming a power-velocity spectrum from received backscattered signal; and d) forming an instantaneous power-velocity integral of laminar flow for the power-velocity spectrum as the integral of power times velocity, said power-velocity integral being proportional to instantaneous flow rate of the laminar flow.

17. A method as claimed in claim 16, including (e) identifying a narrow velocity spectrum of laminar flow to be used in forming the power-velocity integral, said step (e) including:
   (i) smoothing the power-velocity spectrum;
   (ii) determining the velocity of peak power in a smoothed power-velocity spectrum;
   (iii) determining a lower velocity of laminar flow, said lower velocity being a selected velocity less than the velocity for peak power where the power is a specified percentage of the peak power; and
   (iv) determining an upper velocity of laminar flow, said upper velocity being a selected velocity greater than the velocity of peak power where the power is a specified percentage of the peak power.

18. A method as claimed in claim 16, wherein said sample volume is at the vena contracta of flow exiting the orifice.

19. A method as claimed in claim 18, including the step (f) of steering and focusing the ultrasonic signal to said vena contracta.

20. A method as claimed in claim 19, wherein step (f) includes utilizing an image mode display of backscattered signal to steer and focus the signal to the vena contracts, and utilizing at least one of a Doppler mode power/time display and audio signal to fine tune steering/focusing of the ultrasonic signal to the vena contracta.

21. A method as claimed in claim 16, wherein said ultrasonic signal to be used for said power-velocity integral measurement ($PVI_{meas}$) is wide enough to fully ensonify the cross-sectional area of the laminar flow.

22. A method as claimed in claim 16, including repeating steps a), b), c) and d) to obtain a profile of instantaneous flow rates over time.

23. A method as claimed in claim 16, wherein said flow is regurgitant flow though a faulty heart valve, the flow rate being that passing through lesion in the heart valve permitting the regurgitant flow.

24. A method as claimed in claim 16, wherein said flow is stenotic flow through a restricted heart valve, the flow rate being that passing through the restricted valve opening area permitting the flow in normal direction through the valve.

25. A method as claimed in claim 16, wherein said flow is shunt flow through a shunt lesion, the flow rate being that passing through shunt lesions permitting the shunt flow.

26. A method as claimed in claim 16, wherein said flow is stenotic flow through a restricted peripheral vessel, the flow rate being that passing through the restricted area of flow.

27. A method as claimed in claim 16, including the step of (g) of calibrating to permit absolute flow rate to be obtained.

28. A method as claimed in claim 26, wherein step (g) includes applying a narrow ultrasound reference beam within said region, said reference beam having a known CSA ($CSA_{ref}$), and computing Flow rate from Flow rate= $CSA_{ref} \cdot PVI_{meas}/PI_{ref}$.

29. A method as claimed in claim 28, wherein said flow is regurgitant flow through a faulty heart valve, and wherein step (g) includes detecting Doppler ultrasound power from said reference beam when the valve is open for forward flow.

30. A method as claimed in claim 16, wherein said pulsed wave Doppler signal is a high-PRF Doppler signal.

31. A method for obtaining flow volume of blood passing through a dynamic orifice in at least one direction comprising:
   a) ensonifying a sample volume of blood flow exiting the orifice, which volume is in a region of said flow which is substantially laminar, with an ultrasonic pulsed Doppler signal;
   b) receiving backscattered signal from blood within said sample volume;
   c) forming a power-velocity spectrum from received backscattered signal;
   d) forming an instantaneous integral of power times velocity for laminar flow of the power-velocity spectrum;
   e) repeating step (d) to produce a time profile of an instantaneous flow rate; and
   f) forming the time integral of an instantaneous flow rate profile for an interval of time where flow volume is to be measured, said time integral of instantaneous power-velocity integral being proportional to flow volume.

32. A method as claimed in claim 31, including (e) identifying a narrow velocity spectrum of laminar flow to be used in forming the power-velocity integral, said step (e) including:
   (i) smoothing the power-velocity spectrum;
   (ii) determining the velocity of peak power in a smoothed power-velocity spectrum;
   (iii) determining a lower velocity of laminar flow, said lower velocity being a selected velocity less than the velocity for peak power where the power is a specified percentage of the peak power; and
   (iv) determining an upper velocity of laminar flow, said upper velocity being a selected velocity greater than the velocity of peak power where the power is a specified percentage of the peak power.

33. A method as claimed in claim 31, wherein said sample volume is at the vena contracta of flow exiting the orifice.

34. A method as claimed in claim 33, including the step (f) of steering and focusing the ultrasonic signal to said vena contracta.

35. A method as claimed in claim 34, wherein step (f) includes utilizing an image mode display of backscattered signal to steer and focus the signal to the vena contracts, and utilizing at least one of a Doppler mode power/time display and audio signal to fine tune steering/focusing of the ultrasonic signal to the vena contracts.

36. A method as claimed in claim 31, wherein said ultrasonic signal to be used for said power-velocity time integral measurement ($PVTI_{meas}$) is wide enough to fully ensonify the cross-sectional area of the laminar flow.

37. A method as claimed in claim 31, wherein said flow is regurgitant flow though a faulty heart valve, the flow rate being that passing through lesion in the heart valve permitting the regurgitant flow.

38. A method as claimed in claim 31, wherein said flow is stenotic flow through a restricted heart valve, the flow volume being that passing through the restricted valve opening area permitting the flow in normal direction through the valve.

39. A method as claimed in claim 31, wherein said flow is shunt flow through a shunt lesion, the flow volume being that passing through shunt lesions permitting the shunt flow.

40. A method as claimed in claim 31, wherein said flow is stenotic flow through a restricted peripheral vessel, the flow volume being that passing through the restricted area of flow.

41. A method as claimed in claim 31, including the step (h) of calibrating to permit absolute flow volume to be obtained.

42. A method as claimed in claim 41, wherein step (h) includes applying a narrow ultrasound reference beam within said vena contracta, said reference beam having a known CSA ($CSA_{ref}$), and computing Flow volume from Flow volume=$CSA_{ref} \cdot PVTI_{meas}/PI_{ref}$.

43. A method as claimed in claim 42, wherein said flow is regurgitant flow through a faulty heart valve, and wherein step (h) includes detecting Doppler ultrasound power from said reference beam when the valve is open for forward flow.

44. A method as claimed in claim 43, including the step of determining cardiac output, said step including:
    (i) measuring blood flow volume passing through a heart valve orifice in the forward direction;
    (ii) measuring regurgitant blood flow volume passing through the valve orifice in the reverse direction; and
    (iii) summing the measurements of (i) and (ii) so as to provide a measure of the cardiac output.

45. A method as claimed in claim 43, including the step of computing the fraction of reverse versus forward flow, said step including:
    (i) the uncalibrated measuring of blood flow volume passing through the orifice in the forward direction;
    (ii) the uncalibrated measuring of regurgitant blood flow volume passing through the orifice in the reverse direction; and
    (iii) combining the measurements of (i) and (ii) so as to provide a measure of the regurgitant fraction.

46. A method as claimed in claim 31, wherein said pulsed wave Doppler signal is a high-PRF Doppler signal.

47. Apparatus for obtaining an area of a dynamic orifice through which blood is flowing in at least one direction including:
    (a) means for ensonifying a sample volume of blood flow exiting the orifice, which volume is in a region of said flow which is substantially laminar, with an ultrasonic pulsed Doppler signal;
    (b) a receiver for backscattered signal from blood within said sample volume;
    (c) means for forming a power-velocity spectrum from received backscattered signal; and
    (d) means for forming an instantaneous power integral for laminar flow of the power-velocity spectrum, said power integral being proportional to instantaneous cross-sectional area of the orifice.

48. Apparatus as claimed in claim 47, including means for determining the portions of laminar flow in said power velocity spectrum.

49. Apparatus as claimed in claim 48, including means for identifying a narrow velocity spectrum of laminar flow to be used in the power integral calculation, said means including:
    (a) means for smoothing the power-velocity spectrum;
    (b) means for determining the velocity of peak power in a smoothed power-velocity spectrum;
    (c) means for determining a lower velocity of laminar flow, said lower velocity being a selected velocity less than the velocity for peak power where the power is a specified percentage of the peak power; and
    (d) means for determining an upper velocity of laminar flow, said upper velocity being a selected velocity greater than the velocity of peak power where the power is a specified percentage of the peak power.

50. Apparatus as claimed in claim 47, wherein said sample volume is at the vena contracta of flow exiting the orifice.

51. Apparatus as claimed in claim 47, including means for steering and focusing the ultrasonic signal to said vena contracta.

52. Apparatus as claimed in claim 47, wherein said ultrasonic signal to be used for said power integral measurement ($PI_{meas}$) is wide enough to fully ensonify the cross-sectional area of the laminar flow.

53. Apparatus as claimed in claim 47, including means for obtaining a profile of flow area over time by successively operating means a), b), c), and d).

54. Apparatus as claimed in claim 47, wherein said flow is regurgitant flow though a faulty heart valve, the orifice area being that of lesions in the heart valve permitting the regurgitant flow.

55. Apparatus as claimed in claim 47, wherein said flow is stenotic flow through a restricted heart valve, the orifice area measurement being of the restricted valve opening area permitting the flow in normal direction through the valve.

56. Apparatus as claimed in claim 47, wherein said flow is shunt flow through a shunt lesion, the orifice area measurement being of shunt lesions permitting the shunt flow.

57. Apparatus as claimed in claim 47, wherein said flow is stenotic flow through a restricted peripheral vessel, the orifice area measurement being the restricted area of flow.

58. Apparatus as claimed in claim 47, including means for calibrating to permit absolute area of laminar flow to be obtained.

59. Apparatus as claimed in claim 58, including means for applying a narrow ultrasound reference beam within said region, said reference beam having a known CSA ($CSA_{ref}$), and means for computing Flow CSA from Flow CSA=$CSA_{ref} \cdot PI_{meas}/PI_{ref}$.

60. Apparatus as claimed in claim 59, wherein said flow is regurgitant flow through a faulty heart valve, and including means for detecting Doppler ultrasound power from said reference beam when the valve is open for forward flow.

61. Apparatus for obtaining flow rate of blood passing through a dynamic orifice in at least one direction including:
    a) means for ensonifying a sample volume of blood flow exiting the orifice, which volume is in a region of said flow which is substantially laminar, with an ultrasonic pulsed Doppler signal;
    b) a receiver for backscattered signal from blood within said sample volume;
    c) means for forming a power-velocity spectrum from received backscattered signal; and
    d) means for forming an instantaneous power-velocity integral for laminar flow of the power-velocity spectrum as the integral of power times velocity, said power-velocity integral being proportional to instantaneous flow rate of the laminar flow.

62. Apparatus as claimed in claim 61, including means for identifying a narrow velocity spectrum of laminar flow to be used in the power-velocity integral calculation, said means including:
    (a) means for smoothing the power-velocity spectrum;
    (b) means for determining the velocity of peak power in a smoothed power-velocity spectrum;
    (c) means for determining a lower velocity of laminar flow, said lower velocity being a selected velocity less than the velocity for peak power where the power is a specified percentage of the peak power; and
    (d) means for determining an upper velocity of laminar flow, said upper velocity being a selected velocity greater than the velocity of peak power where the power is a specified percentage of the peak power.

63. Apparatus as claimed in claim 61, wherein said sample volume is at the vena contracta of flow exiting the orifice.

64. Apparatus as claimed in claim 63, including means for steering and focusing the ultrasonic signal to said vena contracts.

65. Apparatus as claimed in claim 61, wherein said ultrasonic signal to be used for said power-velocity integral measurement (PVI$_{meas}$) is wide enough to fully ensonify the cross-sectional area of the laminar flow.

66. Apparatus as claimed in claim 61, including means for obtaining a profile of instantaneous flow rates over time by successively operating means a), b), c) and d).

67. Apparatus as claimed in claim 61, wherein said flow is regurgitant flow though a faulty heart valve, the flow rate being that passing through lesion in the heart valve permitting the regurgitant flow.

68. Apparatus as claimed in claim 61, wherein said flow is stenotic flow through a restricted heart valve, the flow rate being that passing through the restricted valve opening area permitting the flow in normal direction through the valve.

69. Apparatus as claimed in claim 61, wherein said flow is shunt flow through a shunt lesion, the flow rate being that passing through shunt lesions permitting the shunt flow.

70. Apparatus method as claimed in claim 61, wherein said flow is stenotic flow through a restricted peripheral vessel, the flow rate being that passing through the restricted area of flow.

71. Apparatus method as claimed in claim 61, including means for calibrating to permit absolute flow rate to be obtained.

72. Apparatus as claimed in claim 71, including means for applying a narrow ultrasound reference beam within said region, said reference beam having a known CSA (CSA$_{ref}$), and computing Flow rate from Flow rate=CSA$_{ref}$·PVI$_{meas}$/PI$_{ref}$.

73. Apparatus as claimed in claim 72, wherein said flow is regurgitant flow through a faulty heart valve, and including means for detecting Doppler ultrasound power from said reference beam when the valve is open for forward flow.

74. A method as claimed in claim 61, wherein said pulsed wave Doppler signal is a high-PRF Doppler signal.

75. Apparatus for obtaining flow volume of blood passing through a dynamic orifice in at least one direction including:
   a) means for ensonifying a sample volume of blood flow exiting the orifice, which volume is in a region of said flow which is substantially laminar, with an ultrasonic pulsed Doppler signal;
   b) means for receiving backscattered signal from blood within said sample volume;
   c) means for forming a power-velocity spectrum from received backscattered signal;
   d) means for forming an instantaneous integral of power times velocity for laminar flow of the power-velocity spectrum;
   e) means for obtaining a time profile of an instantaneous flow rate by successively operating means a) through d); and
   f) means for obtaining the time integral of an instantaneous flow rate profile for that interval of time where flow volume is to be measured, said time integral of instantaneous power-velocity integrals being proportional to flow volume.

76. Apparatus as claimed in claim 75, including means for identifying a narrow velocity spectrum of laminar flow to be used in the power integral calculation, said means including:
   (a) means for smoothing the power-velocity spectrum;
   (b) means for determining the velocity of peak power in a smoothed power-velocity spectrum;
   (c) means for determining a lower velocity of laminar flow, said lower velocity being a selected velocity less than the velocity for peak power where the power is a specified percentage of the peak power; and
   (d) means for determining an upper velocity of laminar flow, said upper velocity being a selected velocity greater than the velocity of peak power where the power is a specified percentage of the peak power.

77. Apparatus as claimed in claim 75, wherein said sample volume is at the vena contracta of flow exiting the orifice.

78. Apparatus as claimed in claim 77, including means for steering and focusing the ultrasonic signal to said vena contracts.

79. Apparatus as claimed in claim 75, wherein said ultrasonic signal to be used for said power-velocity time integral measurement (PVTI$_{meas}$) is wide enough to fully ensonify the cross-sectional area of the laminar flow.

80. Apparatus as claimed in claim 75, wherein said flow is regurgitant flow though a faulty heart valve, the flow rate being that passing through lesion in the heart valve permitting the regurgitant flow.

81. Apparatus as claimed in claim 75, wherein said flow is stenotic flow through a restricted heart valve, the flow volume being that passing through the restricted valve opening area permitting the flow in normal direction through the valve.

82. Apparatus as claimed in claim 75, wherein said flow is shunt flow through a shunt lesion, the flow volume being that passing through shunt lesions permitting the shunt flow.

83. Apparatus as claimed in claim 75, wherein said flow is stenotic flow through a restricted peripheral vessel, the flow volume being that passing through the restricted area of flow.

84. Apparatus as claimed in claim 75, including means for calibrating to permit absolute flow volume to be obtained.

85. Apparatus as claimed in claim 84, including means for applying a narrow ultrasound reference beam within said region, said reference beam having a known CSA (CSA$_{ref}$), and computing Flow volume from Flow volume=CSA$_{ref}$·PVTI$_{meas}$/PI$_{ref}$.

86. Apparatus as claimed in claim 85, wherein said flow is regurgitant flow through a faulty heart valve, and including means for detecting Doppler ultrasound power from said reference beam when the valve is open for forward flow.

87. Apparatus as claimed in claim 86, including means for determining cardiac output, said means including:
   (i) means for measuring blood flow volume passing through a heart valve orifice in the forward direction;
   (ii) means for measuring regurgitant blood flow volume passing through said heart valve orifice in the reverse direction; and
   (iii) means for summing the measurements of (i) and (ii) so as to provide a measure of the cardiac output.

88. Apparatus as claimed in claim 80, including means for computing the fraction of reverse versus forward flow, said means including:
   (i) means for uncalibrated measurement of blood flow volume passing through the orifice in the forward direction;
   (ii) means for uncalibrated measurement of regurgitant blood flow volume passing through the orifice in the reverse direction; and
   (iii) means for combining the measurements of (i) and (ii) so as to provide a measure of the regurgitant fraction.

89. A method as claimed in claim 75, wherein said pulsed wave Doppler signal is a high-PRF Doppler signal.

* * * * *